US009371362B2

(12) United States Patent
Ho

(10) Patent No.: US 9,371,362 B2
(45) Date of Patent: Jun. 21, 2016

(54) PROSTATE SPECIFIC ANTIGEN AGENTS AND METHODS OF USING SAME FOR PROSTATE CANCER IMAGING

(71) Applicant: VisEn Medical, Inc., Waltham, MA (US)

(72) Inventor: Guojie Ho, Sudbury, MA (US)

(73) Assignee: VisEn Medical, Inc., Waltham, MA (US)

( * ) Notice: Subject to any disclaimer, the term of this patent is extended or adjusted under 35 U.S.C. 154(b) by 0 days.

(21) Appl. No.: 13/839,413

(22) Filed: Mar. 15, 2013

(65) Prior Publication Data

US 2014/0050662 A1    Feb. 20, 2014

Related U.S. Application Data

(60) Provisional application No. 61/683,305, filed on Aug. 15, 2012.

(51) Int. Cl.
*C07K 4/00* (2006.01)
*C07K 7/06* (2006.01)
*A61K 49/00* (2006.01)
*G01N 21/64* (2006.01)
*A61K 47/48* (2006.01)

(52) U.S. Cl.
CPC ............. *C07K 7/06* (2013.01); *A61K 47/48338* (2013.01); *A61K 49/0056* (2013.01); *G01N 21/6486* (2013.01)

(58) Field of Classification Search
None
See application file for complete search history.

(56) References Cited

U.S. PATENT DOCUMENTS

| | | |
|---|---|---|
| 4,981,977 A | 1/1991 | Southwick et al. |
| 5,268,486 A | 12/1993 | Waggoner et al. |
| 5,486,616 A | 1/1996 | Waggoner et al. |
| 5,569,587 A | 10/1996 | Waggoner |
| 5,569,766 A | 10/1996 | Waggoner et al. |
| 5,593,658 A | 1/1997 | Bogdanov et al. |
| 5,627,027 A | 5/1997 | Waggoner |
| 5,808,044 A | 9/1998 | Brush et al. |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,083,485 A | 7/2000 | Licha et al. |
| 6,083,486 A | 7/2000 | Weissleder et al. |
| 6,127,134 A | 10/2000 | Minden et al. |
| 6,127,333 A | 10/2000 | Brady et al. |
| 6,130,094 A | 10/2000 | Waggoner et al. |
| 6,130,204 A | 10/2000 | DeFeo-Jones et al. |
| 6,133,445 A | 10/2000 | Waggoner et al. |
| 6,136,612 A | 10/2000 | Della Ciana et al. |
| 6,174,858 B1 * | 1/2001 | Brady et al. .................... 514/1.3 |
| 6,177,404 B1 | 1/2001 | DeFeo-Jones et al. |
| 6,258,340 B1 | 7/2001 | Licha et al. |
| 6,391,305 B1 | 5/2002 | Feng et al. |
| 6,448,008 B1 | 9/2002 | Caputo et al. |
| 6,534,041 B1 | 3/2003 | Licha et al. |
| 6,592,847 B1 | 7/2003 | Weissleder et al. |
| 6,740,755 B2 | 5/2004 | Caputo et al. |
| 6,747,159 B2 | 6/2004 | Caputo et al. |
| 6,869,593 B2 | 3/2005 | Frangioni |
| 6,913,743 B2 | 7/2005 | Licha et al. |
| 6,926,885 B2 | 8/2005 | Licha et al. |
| 7,025,949 B2 | 4/2006 | Licha et al. |
| 7,371,728 B2 | 5/2008 | Wang et al. |
| 7,374,746 B2 | 5/2008 | Frangioni |
| 7,445,767 B2 | 11/2008 | Licha et al. |
| 7,655,217 B2 | 2/2010 | Licha et al. |
| 7,947,256 B2 | 5/2011 | Rajopadhye et al. |
| 8,173,819 B2 | 5/2012 | Rajopadhye et al. |
| 8,221,721 B2 | 7/2012 | Narayanan |
| 8,420,055 B2 | 4/2013 | Gaw et al. |
| 8,455,651 B2 | 6/2013 | Rajopadhye et al. |
| 8,486,373 B2 | 7/2013 | Weissleder et al. |
| 8,685,370 B2 | 4/2014 | Rajopadhye et al. |
| 8,771,646 B2 | 7/2014 | Rajopadhye et al. |
| 8,815,214 B2 | 8/2014 | Rajopadhye et al. |
| 2005/0169843 A1 | 8/2005 | Weissleder et al. |
| 2006/0154324 A1 | 7/2006 | Wang et al. |
| 2007/0244055 A1 | 10/2007 | Brady et al. |
| 2008/0226562 A1 | 9/2008 | Groves et al. |
| 2009/0130024 A1 | 5/2009 | Narayanan et al. |
| 2010/0074847 A1 | 3/2010 | Madden et al. |
| 2010/0166659 A1 | 7/2010 | Licha et al. |
| 2010/0172841 A1 | 7/2010 | Peterson et al. |
| 2010/0189657 A1 | 7/2010 | Weissleder et al. |

(Continued)

FOREIGN PATENT DOCUMENTS

| | | |
|---|---|---|
| EP | 1065250 A1 | 1/2001 |
| WO | WO-97/40104 | 10/1997 |

(Continued)

OTHER PUBLICATIONS

Williams et al (Prostate, 2011, 71(15): 1595-1607).*
Alfano et al., "Advances in Optical Imaging of Biomedical Media," *Ann. NY Acad Sci.*, vol. 820, pp. 248-271 (1997).
Citrin et al., "Optical imaging of mice in oncologic research," *Expert Rev. Anticancer Ther.*, vol. 4, pp. 857-864 (2004).
Drake et al., "Activatable Optical Probes for the Detection of Enzymes," *Curr. Org. Synth.*, vol. 8, pp. 498-520 (2011).
Graves et al., "Fluorescence Molecular Imaging of Small Animal Tumor Models," *Current Molecular Medicine*, vol. 4, pp. 419-430 (2004).
International Search Report and Written Opinion for International Application No. PCT/US2013/032200, mailed Aug. 6, 2013 (13 pages).

(Continued)

*Primary Examiner* — Sean Aeder
(74) *Attorney, Agent, or Firm* — Goodwin Procter LLP

(57) ABSTRACT

The invention provides a family of agents that target the prostate specific antigen, which can be used as imaging agents or therapeutic agents. The agents can be used to image prostate cancer as well as other physiological processes in a subject.

12 Claims, 3 Drawing Sheets
(3 of 3 Drawing Sheet(s) Filed in Color)

(56) References Cited

U.S. PATENT DOCUMENTS

| | | |
|---|---|---|
| 2010/0268070 A1 | 10/2010 | Jaffer et al. |
| 2011/0152501 A1 | 6/2011 | Weissleder et al. |
| 2011/0171136 A1 | 7/2011 | Poss et al. |
| 2011/0256065 A1 | 10/2011 | Frangioni |
| 2012/0321563 A1 | 12/2012 | Groves et al. |
| 2013/0137873 A1 | 5/2013 | Narayanan |
| 2014/0050662 A1 | 2/2014 | Ho |

FOREIGN PATENT DOCUMENTS

| | | |
|---|---|---|
| WO | WO-99/51702 | 10/1999 |
| WO | WO-01/21624 | 3/2001 |
| WO | WO-2007/028037 | 3/2007 |
| WO | WO-2007/028163 | 3/2007 |
| WO | WO 2007/028163 A1 * | 3/2007 |
| WO | WO-2009/092062 | 7/2009 |
| WO | WO 2009/092062 A2 * | 7/2009 |
| WO | WO-2011/146143 | 11/2011 |

OTHER PUBLICATIONS

Koo et al., "Non-invasive in vivo imaging in small animal research," *Cell. Oncol.* vol. 28, pp. 127-139 (2006).

Ntziachristos et al., "Fluorescence imaging with near-infrared light: new technological advances that enable in vivo molecular imaging," *Eur. Radiol.*, vol. 13, pp. 195-208 (2003).

Ntziachristos, "Fluorescence Molecular Imaging," *Ann. Rev. Biomed. Eng.*, vol. 8, pp. 1-33 (2006).

Ozmen et al., "Infrared fluorescence sensing of submicromolar calcium: pushing the limits of photoinduced electron transfer," *Tetrahedron Letters*, vol. 41, pp. 9185-9188 (2000).

Rao et al., "Fluorescence imaging in vivo: recent advances," *Curr. Opin. Biotechnol.*, vol. 18, pp. 17-25 (2007).

Weissleder, "A clearer vision for in vivo imaging," *Nature Biotechnology*, vol. 19, pp. 316-317 (2001).

Ho et al. (2013) "Detection and quantification of enzymatically active prostate-specific antigen in vivo," *Journal of Biomedical Optics* 18(10):101319-1 to 101319-8.

* cited by examiner

PROSTATE SPECIFIC ANTIGEN AGENTS AND METHODS OF USING SAME FOR PROSTATE CANCER IMAGING

RELATED APPLICATIONS

This application claims the benefit of and priority to U.S. Provisional Patent Application No. 61/683,305, filed Aug. 15, 2012, the contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Jun. 21, 2013, is named VIS-045_SL.txt and is 14,703 bytes in size.

FIELD OF THE INVENTION

The invention provides compositions and methods for detecting prostate cancer in a subject. The compositions generally contain a prostate specific antigen targeting moiety and an imaging reporter, which may be a fluorophore.

BACKGROUND

Current approaches for assessing molecular endpoints in certain diseases usually require tissue and blood sampling, surgery, and in the case of experimental animals, sacrifice at different time points. Despite improvements in non-invasive imaging, more sensitive and specific imaging agents and methods are needed. Imaging techniques capable of visualizing specific molecular targets and/or entire pathways would significantly enhance our ability to diagnose and assess treatment efficacy of therapeutic interventions for many different disease states. Most current imaging techniques report primarily on anatomical or physiological information (e.g., magnetic resonance imaging (MRI), computed tomography (CT), and ultrasound). Newer modalities such as optical imaging and new molecular imaging probes have the potential to revolutionize the way disease is detected, treated, and monitored.

A common paradigm for molecular imaging involves the use of a "molecular" probe or agent that selectively targets a particular gene, protein, receptor or a cellular function, with the absence, presence, or level of the specific target being indicative of a particular disease state. In particular, optical imaging offers several advantages that make it a powerful molecular imaging approach, both in the research and clinical settings. Optical imaging can be fast, safe, cost effective, and highly sensitive. Scan times are on the order of seconds to minutes, there is no need for ionizing radiation, and the imaging systems can be simple to use. In addition, optical probes can be designed as dynamic molecular imaging agents that may alter their reporting profiles in vivo to provide molecular and functional information in real time. In order to achieve maximum penetration and sensitivity in vivo, the choice for most optical imaging in biological systems is within the red and near-infrared (NIR) spectral region (600-900 nm), although other wavelengths in the visible region can be used. In the NIR wavelength range, absorption by physiologically abundant absorbers such as hemoglobin or water, as well as tissue autofluorescence, is minimized.

Prostate cancer is the sixth leading cause of cancer-related death in the world; it is the second leading cause of cancer-related death in the United States. Prostate cancer develops in the prostate, a gland of the male reproductive system. While it can be aggressive, most forms are slow growing cancers. Metastasis, or spreading, of the cancer may occur in other parts of the body such as the bones and lymph nodes. Prostate cancer can cause symptoms such as difficulty during urination, frequent urination, increased nighttime urination, blood in the urine, painful urination, erectile dysfunction, problems during sexual intercourse, and pain.

Prostate Specific Antigen (PSA) is a protein produced by cells of the prostate gland. PSA was the first identified prostate antigen and has become a premier tumor marker for diagnosis, monitoring, and prognosis of prostatic carcinoma. Prostate specific antigen serves as a molecular target for novel active and passive immunotherapy currently under investigation.

PSA is not found in significant levels in tissues outside the prostate gland. Under normal conditions, high concentrations of PSA are stored in the prostatic ductal network. Disruption of the normal tissue architecture in the prostate or distal sites by prostate cancer cells causes leakage of increased amounts of PSA into the tissue interstitium and then the circulation.

Though PSA is used to screen for prostate cancer, a patient's serum PSA level alone does not provide enough information to distinguish benign prostate conditions from actual cancer of the prostate. Furthermore, there are several issues regarding the use of PSA as a target for therapy. First, it is secreted and present in high concentrations in the serum. This can block targeting to tumor cells before a therapeutic or diagnostic agent can bind or enter the cancer cell. Second, PSA is expressed at lower levels in hormone-resistant cancer.

One complication to effective prostate cancer screening is the existence of multiple forms of the PSA protein. Within the prostate, peptidases remove amino acid sequences from the immature PSA protein to create the mature, enzymatically active form of the PSA protein. Enzymatically active PSA is only present in prostate tissue. Enzymatically inactive variants of PSA are created when the immature protein is not properly processed. Standard diagnostic tests do not distinguish between enzymatically active and inactive forms of PSA. Small quantities of enzymatically active PSA leak out of the prostatic ductal network into circulation. High serum levels of the enzymatically active form of PSA are only found during prostate cancer. Once in circulation, the active PSA forms complexes with the serum protease inhibitor alpha-1-antichymotrypsin (ACT), while the enzymatically inactive forms remain unbound. The combined totals contribute to the low levels that can be measured in the circulation. High levels of complexed (and therefore enzymatically active) PSA are more likely indicative of the presence of cancer. Targeting the enzymatically active form of PSA would lead to more reliable prostate cancer diagnoses.

Long term survival from cancer is highly dependent upon early detection and treatment. The ability to detect different patterns of protein expression in healthy versus abnormal prostate tissue can help classify early prostate changes that could lead to cancer. The ability to more accurately and efficiently detect and quantify levels of mature prostate specific antigen will aid in the understanding of pathogenesis and prognosis of prostate cancer, as well as in the determination of the most appropriate treatment regimens.

SUMMARY OF THE INVENTION

The invention provides fluorescent imaging agents activated only by the enzymatically active prostate specific antigen, and these agents can be used in a variety of in vitro and in vivo applications, including but not limited to, screening for prostate cancer. Also provided are agents/ligands that are fluorescent, upon activation, in the far-red or near-infrared region that are of particular utility for in vivo imaging of prostate cancer in humans. In addition, agents are provided that, independently, contain a far-red or near-infrared fluorophore that has been modified by a plurality of chemical modifying groups that can be used for optimization of in vitro and in vivo properties of the agent.

Accordingly, one aspect of the invention provides a prostate specific antigen activatable agent, wherein the agent comprises (i) a prostate specific antigen targeting moiety comprising an enzymatically cleavable oligopeptide sequence; (ii) two or more imaging reporter moieties chemically linked, optionally through a linker (L) moiety to the prostate specific antigen targeting moiety; and (iii) an optional Pharmacokinetic (PK) modifier chemically linked to the prostate specific antigen targeting moiety. In certain embodiments, the imaging reporter is a fluorescent moiety. In yet other embodiments, imaging reporter bears a plurality of chemical modifying moieties.

In certain embodiments, the prostate specific antigen activatable agent is represented by Formula (I) or a salt thereof:

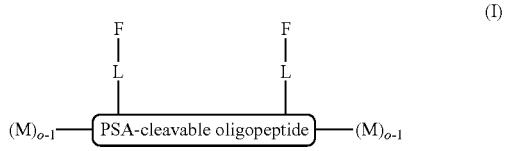

(I)

wherein F is a fluorophore or a quencher molecule, L is a bond or a linker; and M is a modifier, attached to either C or N terminus, or both, of the oligopeptide.

In certain embodiments, the agent, upon activation by prostate specific antigen, is fluorescent in the far-red or near-infrared wavelengths.

In certain embodiments, the PSA-cleavage oligopeptide is a radical of an oligopeptide listed in Table 1.

TABLE 1

Exemplary Enzymatically Cleavable Oligopeptide Sequences

| Oligopeptide | SEQ ID NO |
|---|---|
| Ac-Lys-Hyp-Ser-Ser-Chg-Gln-Ser-Ser-Lys-NH$_2$ | 1 |
| Gly-Hyp-Ala-Ser-Chg-Gln-Ser-Ser-Lys-NH$_2$ | 2 |
| Gly-Hyp-Ala-Ser-Chg-Gln-Ser-Ser-Lys | 3 |
| Hyp-Ser-Ser-Chg-Gln-Ser-Ser-Lys | 4 |
| Ac-Lys-Hyp-Ser-Ser-Chg-Gln-Ser-Ser-Lys | 5 |
| Ac-Lys-Hyp-Ala-Ser-Chg-Gln-Ser-Ser-Lys | 6 |
| Gly-Ser-Ser-Chg-Gln-Ser-Ser-Lys | 7 |
| Gly-Ser-Ser-Phe-Gln-Ser-Ser-Lys | 8 |
| Ac-Lys-Ala-Ser-Phe-Gln-Ser-Leu-Lys | 9 |
| Hyp-Ser-Chg-Gln-Ser-Lys | 10 |
| Ac-Lys-Hyp-Ser-Ser-Phe-Gln-Ser-Ser-Lys | 11 |
| Gly-Ala-Ser-Chg-Gln-Ser-Ser-Lys | 12 |
| Gly-Hyp-Ser-Ser-Chg-Gln-Ser-Ser-Lys | 13 |

In certain embodiments, M is selected from the group consisting of a hydrogen, alcohol, sulfonate, polysulfonate, cysteic acid, sulfonamide, sulfoxide, sulfone, carboxylate, ketone, phosphonate, phosphate; iminodiacetate, ethylenediamine tetraacetic acid, diethylenetriamine pentaacetic acid, tetraazacyclododecane tetraacetic acid, an amino acid or polyamino acid, oligo- or polyethylene glycol, amine, quaternary ammonium ion, sugars, glucosamine, galactosamine, mannosamine, polyethylene glycol (PEG) and derivatives thereof, for example, alkoxy polyethylene glycol (for example, methoxypolyethylene glycol, ethoxypolyethylene glycol and the like), branched polypropylene glycol, polypropylene glycol, a graft copolymer of poly-lysine and methoxypolyethyleneglycol, peptides, lipids, fatty acids, palmitate, phospholipids, phospholipid-PEG conjugates, carbohydrates (such as dextran, amino-dextran, carboxymethyl-dextran), polyvinylpyrrolidone, iron oxide nanoparticles, naphthylalanine, phenylalanine, 3,3-diphenylpropylamine, taurine, phosphonates, phosphates, carboxylates and polycarboxylates.

In certain embodiments, the bond or linker (L) moiety comprises a divalent radical of a moiety selected from the group consisting of glycine, alanine, β-alanine, —NH—(CH$_2$)$_n$—C(=O)— where n=1-8, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, and diamine-amino acids, such as homolysine, lysine, ornithine, diaminobutyric acid and diaminopropionic acid, succinic acid, glutaric acid, suberic acid, adipic acid, amide, triazole, urea, or thiourea.

In certain embodiments, the chemical modifier(s) M improves the stability, the pharmacokinetics or biodistribution of the agent when administered to a live animal.

In certain embodiments, the compound is one of the following or a salt thereof:

5
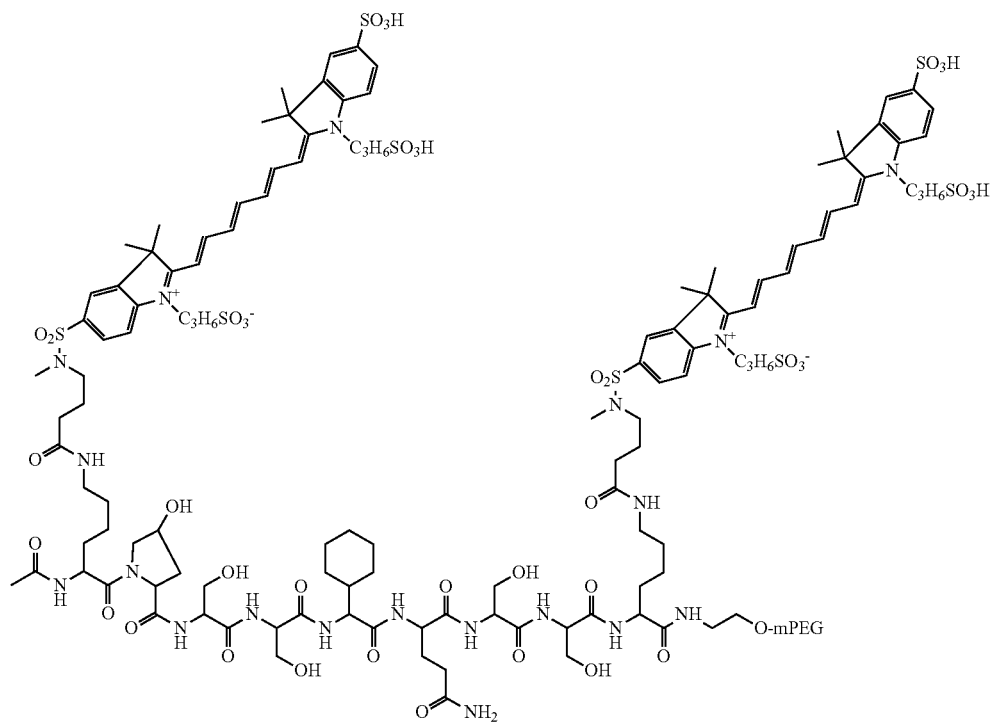
6
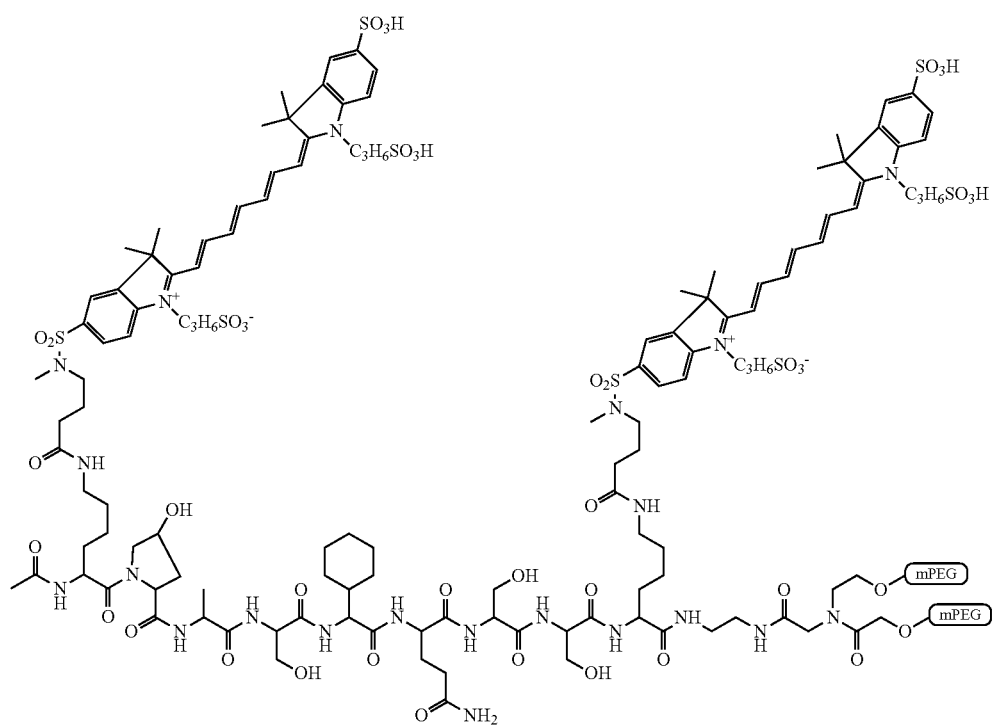

-continued

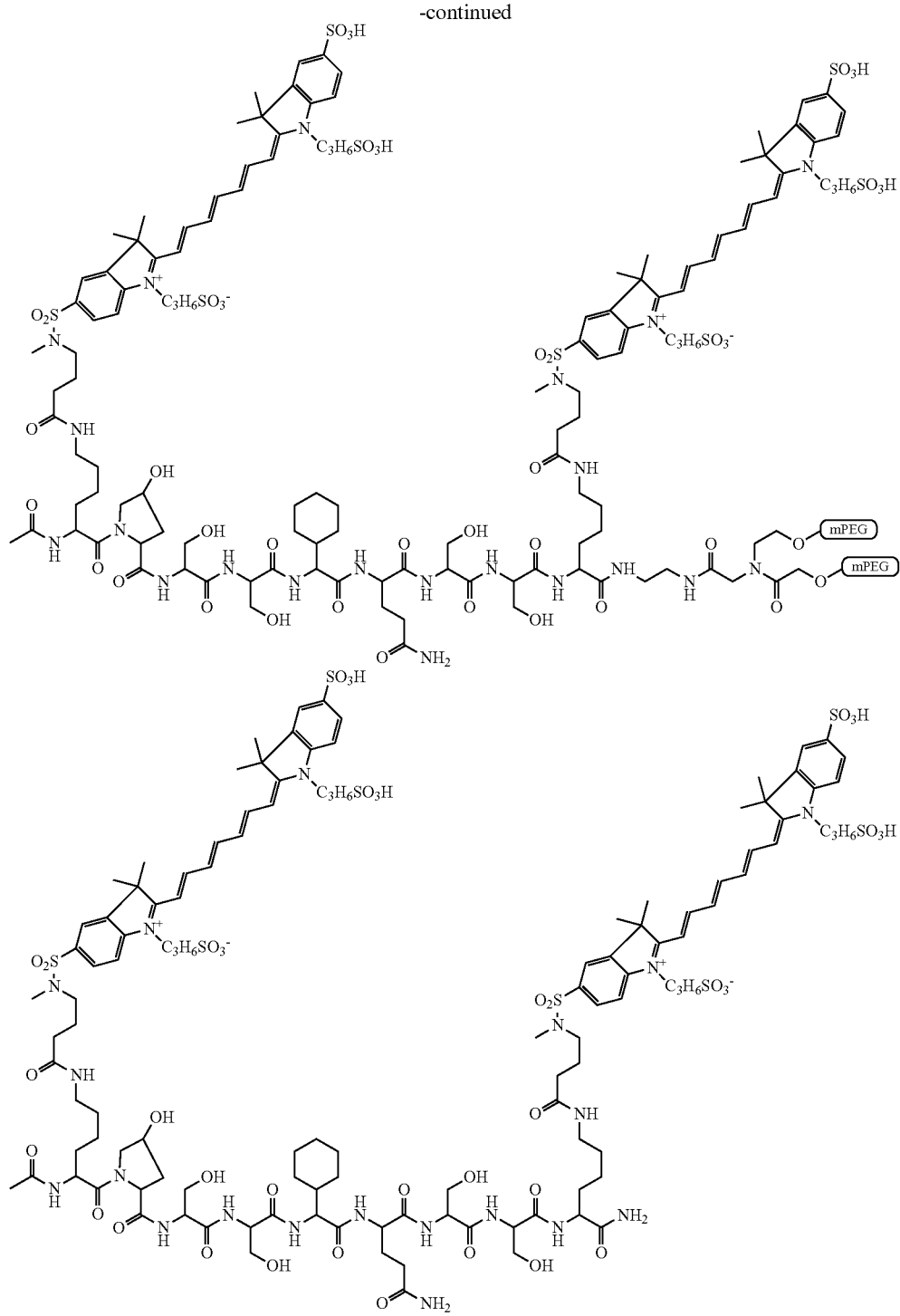

or a compound from Table 4.

Additional exemplary prostate specific antigen activatable agents include compounds embraced by Formulae I and II described in the detailed description.

Another aspect of the invention provides a pharmaceutical composition comprising a prostate specific antigen activatable agent and a pharmaceutically acceptable excipient.

Another aspect of the invention provides method of in vivo imaging, comprising: (a) administering to a subject an agent; (b) allowing the agent to distribute within the subject; and (c) detecting a signal emitted by the prostate specific antigen activatable agent.

Another aspect of the invention provides a method of in vivo optical imaging, the method comprising: (a) administering to a subject an agent, wherein the agent comprises a fluorochrome; (b) allowing the agent to distribute within the subject; (c) exposing the subject to light of a wavelength absorbable by the fluorochrome; and (d) detecting a signal emitted by the agent.

Another aspect of the invention provides a method of in vivo imaging, wherein the signal emitted by the agent is used to construct an image. In other embodiments, the image is a tomographic image. Another aspect of the invention provides a method of in vivo optical imaging, wherein steps (a)-(c) described above are repeated at predetermined time intervals thereby to permit evaluation of the emitted signals of the agent (such as a prostate specific antigen imaging agent) in the subject over time. Another aspect of the invention provides a method of in vivo optical imaging, wherein steps (a)-(d) described above are repeated at predetermined time intervals thereby to permit evaluation of the emitted signals of the agents (such as prostate specific antigen imaging agents) in the subject over time. Another aspect of the invention provides a method of in vivo imaging, wherein the subject is an animal or a human. Another aspect of the invention provides a method of in vivo imaging, wherein in step (a) two or more imaging probes whose signal properties are distinguishable from one another are administered to a subject, wherein at least one of the imaging probes is an agent described herein (such as a prostate specific antigen imaging agent).

Another aspect of the invention provides a method of in vivo optical imaging, wherein the illuminating and detecting steps are performed using an endoscope, catheter, tomographic system, hand-held optical imaging system, or an intraoperative microscope. In certain embodiments, the method is a method of in vivo imaging, wherein the presence, absence, or level of emitted signal is indicative of a disease state. In certain embodiments, the method is a method of in vivo imaging, wherein the method is used to detect and/or monitor a disease. In certain embodiments, the disease is selected from the group consisting of dysplasia, neoplasia, and cancer.

Another aspect of the invention provides a method of in vivo imaging, wherein, in step (a), cells labeled with an agent described herein (such as a prostate specific antigen imaging agent) are administered to the subject. In other embodiments, the signal emitted by the agent (such as a prostate specific antigen imaging agent) is used to monitor trafficking and localization of the cells.

Another aspect of the invention provides a method of imaging prostate cancer in a subject, the method comprising the steps of: (a) administering an agent to a subject; and (b) detecting the presence of the agent thereby to produce an image representative of prostate cancer.

Another aspect of the invention provides a method of treating a disease in a subject comprising administering to a subject, either systemically or locally, an agent, wherein the agent comprises a radiolabel that localizes in the disease area and delivers an effective dose of radiation.

Another aspect of the invention provides an in vitro imaging method, the method comprising: (a) contacting a sample with an agent; (b) allowing the agent to bind to a biological target; (c) optionally removing unbound agent; and (d) detecting signal emitted from the agent thereby to determine whether the agent has been activated by or bound to the biological target. In certain embodiments, the sample is a biological sample.

Compounds described herein are understood to be efficacious for the binding of prostate specific antigen, as well as for in vitro and in vivo fluorescence imaging of prostate cancer and therefore can be used for both therapeutic and diagnostic applications.

In addition, the invention provides methods for in vitro and in vivo imaging using the fluorescent prostate specific antigen imaging agents. With respect to optical in vivo imaging, the method comprises (a) administering to a subject prostate specific antigen activatable agents of the invention; (b) allowing the prostate specific antigen activatable agents to distribute within the subject; (c) exposing the subject to light of a wavelength absorbable by the fluorophore of the prostate specific antigen activatable agent; and (d) detecting an optical signal emitted by the prostate specific antigen activatable agent. The signal emitted by the agent can be used to construct an image. In certain embodiments, certain of the images are a tomographic image. Furthermore, it is understood that the foregoing steps can be repeated at predetermined intervals thereby permitting evaluation of the subject over time.

The prostate specific antigen activatable agents can be formulated into a pharmaceutical composition suitable for administration to a subject, for example, an animal and/or a human subject. The pharmaceutical composition can include one or more of the prostate specific antigen activatable agents and one or more stabilizers in a physiologically acceptable carrier.

The subject may be a vertebrate, for example, a mammal, for example, a human. The subject may also be a non-vertebrate (for example, *C. elegans, Drosophila*, or another model research organism, etc.) used in laboratory research.

In certain embodiments, the fluorophores can be chosen, for example, from a series of fluorescent reporters.

In addition, another aspect of the invention provides methods for in vitro and in vivo imaging using the prostate specific antigen activatable agents. With respect to optical in vivo imaging, one exemplary method comprises (a) administering to a subject one or more of the foregoing prostate specific antigen activatable agents described here, wherein the agents comprise two or more fluorochromes; (b) allowing the agent to distribute within the subject; (c) exposing the subject to light of a wavelength absorbable at least one fluorochrome; and (d) detecting a signal emitted by the prostate specific antigen activatable agent. The signal emitted by the agent can be used to construct an image, for example, a tomographic image. Furthermore, it is understood that the foregoing steps can be repeated at predetermined intervals, which permit evaluation of the subject over time.

The prostate specific antigen activatable agents can be used to measure levels of enzymatically active prostate specific antigen (prostate cancer) or other physiological processes such as cancer in a subject. One exemplary method comprises (a) administering one or more of the foregoing prostate specific antigen activatable agents to a subject; (b) detecting the presence of the agent(s) thereby to produce an image representative of sites of prostate specific antigen activity within the subject.

In each of the foregoing methods, the subject can be a vertebrate, for example, a mammal, for example, a human. The subject also can be a non-vertebrate (for example, *C. elegans, Drosophila*, or another model research organism, etc.) used in laboratory research.

In addition, the prostate specific antigen activatable agents can be incorporated into a kit, for example, a kit with optional instructions for using the prostate specific antigen activatable agents in in vivo or in vitro imaging methods. The kit optionally can include components that aid in the use of the prostate specific antigen activatable agents, for example, buffers, and other formulating agents. Alternatively, the kit can include medical devices that aid in the administration and/or detection of the prostate specific antigen activatable agents to subjects.

Other features and advantages of the invention will be apparent from the following figures, detailed description, and the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
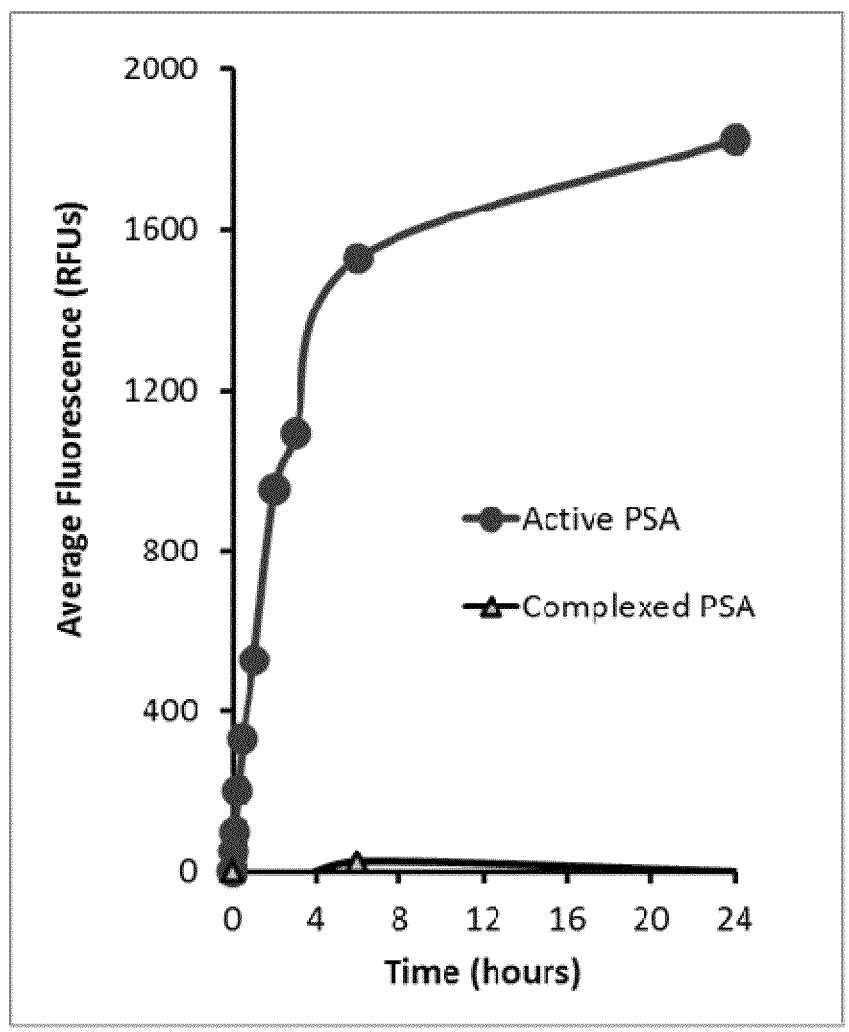
FIG. 1 is a scatter plot comparing the fluorescence of the prostate specific antigen activatable agents when incubated with active PSA versus inactive (complexed) PSA. Data in FIG. 1 depict activation of the prostate specific antigen activatable agents (compound A10).

The invention provides compositions and methods for detecting prostate specific antigen in a subject. Technology described herein is based, in part, upon the discovery that it is possible to produce fluorescent prostate specific antigen activatable agents that are stable, biocompatible, exhibit low nonspecific cellular uptake in vitro, and low nonspecific tissue uptake in vivo, and can be used in a variety of in vitro and in vivo assays and imaging applications, as well as in a variety of therapeutic applications. Various aspects of the prostate specific antigen activatable agents and their use are described in the section below. Aspects of the invention described in one particular section are not to be limited to any particular section. Further, if a variable is not accompanied by a definition, then the previous definition of the variable controls.

I. PROSTATE SPECIFIC ANTIGEN ACTIVATABLE AGENTS

One aspect of the invention provides prostate specific antigen activatable agents. The prostate specific antigen activatable agents generally comprise (i) a prostate specific antigen targeting moiety and (ii) an imaging reporter, which may be a fluorophore. The prostate specific antigen targeting moiety may be connected to the imaging reporter (e.g., a fluorophore) via a linker.

Properties of the prostate specific antigen activatable agent may be adjusted by selecting particular types of imaging reporter moieties, linker, and prostate specific antigen targeting moieties. In addition, properties of the prostate specific antigen activatable agent can be adjusted by attaching one or more chemical modifying group (M). The prostate specific antigen targeting moiety, linker, fluorophore, and chemical modifying moieties are described in more detail in the subsections below.

The "imaging reporter" or "F" can be any suitable chemical or substance which is used to provide the contrast or signal in imaging and that is detectable by imaging techniques. In certain embodiments, the imaging reporter comprises one or more fluorophores or photoluminescent nanoparticles.

The term "chemical modifying group" or "M" is understood to mean any moiety that can be used to alter the physical, chemical or biological properties of the prostate specific antigen activatable agent, such as, without limitations, making it more water soluble or more dispersible in media for administration, increasing binding specificity, increasing or decreasing net molecular charge, decreasing immunogenicity or toxicity, or modifying cell uptake, pharmacokinetic or biodistribution profiles compared to the non-M modified prostate specific antigen activatable agents.

Additional information in prostate specific antigen activatable agents can be found in, for example, U.S. Pat. Nos. 7,371,728; 6,127,333; 6,174,858; 6,391,305; 6,177,404; and 6,130,204; and U.S. Patent Application No. 20070244055, all of which are incorporated herein by reference in their entirety.

A. Prostate Specific Antigen Targeting Moiety

The prostate specific antigen targeting moiety is generally an enzymatically cleavable oligopeptide sequence. Exemplary prostate specific antigen targeting moieties include a radical the following oligopeptide sequences (also described at least in part in Table 1 above):

```
                                            (SEQ ID NO: 3)
    Gly-Hyp-Ala-Ser-Chg-Gln-Ser-Ser-Lys;

(SEQ ID NO: 4)
    Hyp-Ser-Ser-Chg-Gln-Ser-Ser-Lys;

(SEQ ID NO: 5)
    Ac-Lys-Hyp-Ser-Ser-Chg-Gln-Ser-Ser-Lys;

(SEQ ID NO: 6)
    Ac-Lys-Hyp-Ala-Ser-Chg-Gln-Ser-Ser-Lys;

(SEQ ID NO: 7)
    Gly-Ser-Ser-Chg-Gln-Ser-Ser-Lys;
    and (SEQ ID NO: 8)
    Gly-Ser-Ser-Phe-Gln-Ser-Ser-Lys.
```

B. Imaging Reporters

A variety of fluorophores, for example, fluorescent reporters are contemplated to be amenable for use in the present invention. Exemplary fluorophores are described below. The fluorophores may be substituted with a plurality of chemical modifying moieties.

(a) Fluorescent Reporters

In certain embodiments, the imaging reporter is a fluorophore molecule. A "fluorophore" includes, but is not limited to, a fluorochrome, a fluorochrome quencher molecule, any organic or inorganic dye, metal chelate, or any fluorescent enzyme substrate, including protease activatable enzyme substrates.

In certain embodiments, the prostate specific antigen activatable agents comprise a fluorophore. In certain embodiments, the fluorophores are far red and near infrared fluorochromes (NIRFs) with absorption and emission maximum between about 600 and about 1200 nm, more preferably between about 600 nm and about 900 nm. It will be appreciated that the use of fluorochromes with excitation and emission wavelengths in other spectrums can also be employed in the compositions and methods of the present invention. Exemplary fluorochromes include but are not limited to a carbocyanine fluorochrome and an indocyanine fluorochrome.

The far red to near infrared fluorochromes preferably have an extinction coefficient of at least 50,000 $M^{-1}$ $cm^{-1}$ per fluorochrome molecule in aqueous medium. Fluorochromes preferably also have (1) high quantum yield (i.e., quantum yield greater than 5% in aqueous medium), (2) narrow excitation/emission spectrum, spectrally separated absorption and emission spectra (i.e., excitation and emission maxima separated by at least 15 nm), (3) high chemical and photostability, (4) non-toxicity, (5) good biocompatibility, biodegradability and excretability, and (6) commercial viability and scalable production for large quantities (i.e., gram and kilogram quantities) required for in vivo and human use.

Certain carbocyanine or polymethine fluorescent dyes can be used to produce the prostate specific antigen activatable agents of the invention and include, for example, those described in U.S. Pat. No. 6,747,159; U.S. Pat. No. 6,448,008; U.S. Pat. No. 6,136,612; U.S. Pat. Nos. 4,981,977; 5,268,486; U.S. Pat. No. 5,569,587; U.S. Pat. No. 5,569,766; U.S. Pat. No. 5,486,616; U.S. Pat. No. 5,627,027; U.S. Pat. No. 5,808,044; U.S. Pat. No. 5,877,310; U.S. Pat. No. 6,002,003; U.S. Pat. No. 6,004,536; U.S. Pat. No. 6,008,373; U.S. Pat. No. 6,043,025; U.S. Pat. No. 6,127,134; U.S. Pat. No. 6,130,094; U.S. Pat. No. 6,133,445; also WO 97/40104, WO 99/51702, WO 01/21624, and EP 1 065 250 A1; and *Tetrahedron Letters* 41, 9185-88 (2000).

Various fluorochromes are commercially available and can be used to construct the prostate specific antigen activatable agents of the invention. Exemplary fluorochromes include, for example, Cy5.5, Cy5 and Cy7 (GE Healthcare); AlexaFlour660, AlexaFlour680, AlexaFluor750, and AlexaFluor790 (Invitrogen); VivoTag680, VivoTag-S680, and VivoTag-S750 (PerkinElmer); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health).

Table 2 lists a number of exemplary commercial fluorochromes useful in the practice of the invention together with their spectral properties.

TABLE 2

| Fluorochrome | $\epsilon_{max} M^{-1} cm^{-1}$ | Absorbance max (nm) |
|---|---|---|
| Cy5 | 250,000 | 649 |
| Cy5.5 | 250,000 | 675 |
| Cy7 | 250,000 | 743 |
| AlexaFlour660 | 132,000 | 663 |
| AlexaFlour680 | 184,000 | 679 |
| AlexaFlour750 | 280,000 | 749 |
| VivoTag680 (VT680) | 100,000 | 670 |
| VivoTag-S680 | 220,000 | 674 |
| VivoTag-S750 | 100,000 | 750 |
| Dy677 | 180,000 | 673 |
| Dy682 | 140,000 | 690 |
| Dy752 | 270,000 | 748 |
| Dy780 | 170,000 | 782 |
| DyLight547 | 150,000 | 557 |
| DyLight647 | 250,000 | 653 |
| IRDye800CW | 240,000 | 774 |
| IRDye800RS | 200,000 | 767 |
| IRDye700DX | 165,000 | 689 |
| ADS780WS | 170,000 | 782 |
| ADS830WS | 240,000 | 819 |
| ADS832WS | 190,000 | 824 |

In certain embodiments, the fluorophore is substituted by a plurality of chemical modifying groups. In certain embodiments, the fluorophore is represented by formula A:

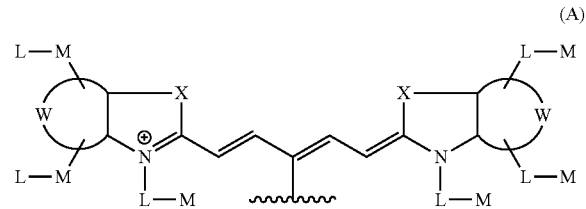

(A)

or a salt thereof, wherein:

W represents a benzo-condensed, a naphtho-condensed or a pyrido-condensed ring;

X, independently for each occurrence, is selected from the group consisting of $C(CH_2Y_1)(CH_2Y_2)$, O, S, and Se;

$Y_1$ and $Y_2$ are independently selected from the group consisting of H, $C_1$-$C_{20}$ aliphatic group, and optionally substituted with L-M;

L, independently for each occurrence, represents a bond or a linker moiety; and

M, independently for each occurrence, represents a modifying moiety.

In certain other embodiments, the fluorophore is represented by Formula B:

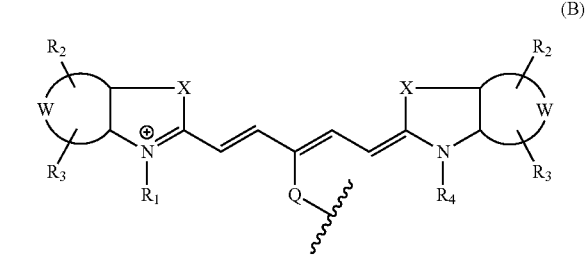

(B)

or a salt thereof, wherein:

X is independently selected from the group consisting of $C(CH_2Y_1)(CH_2Y_2)$, O, S, and Se;

$Y_1$ and $Y_2$ are independently selected from the group consisting of H, $C_1$-$C_{20}$ aliphatic group and a $C_1$-$C_{20}$ aliphatic group substituted with —OR*, N(R*)$_2$ or —SR*;

W represents a benzo-condensed, a naphtho-condensed or a pyrido-condensed ring;

R* is alkyl;

$R_1$ is selected from the group consisting of —(CH$_2$)$_x$CH$_3$, —(CH$_2$)$_n$SO$_3^-$ and —(CH$_2$)$_n$SO$_3$H, wherein x is an integer selected from 0 to 6 and n is an integer selected from 2 to 6;

$R_4$ is selected from the group consisting of —(CH$_2$)$_x$CH$_3$, —(CH$_2$)$_n$SO$_3^-$ and —(CH$_2$)$_n$SO$_3$H, wherein x is an integer selected from 0 to 6 and n is an integer selected from 2 to 6;

$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is -arylene-C(O)N(R)—(C$_{1-8}$ alkylene)C(O)— where the arylene group is covalently bonded to the alkenylene core of Formula B; and R is hydrogen or alkyl.

In certain other embodiments, the fluorophore is represented by formula B1:

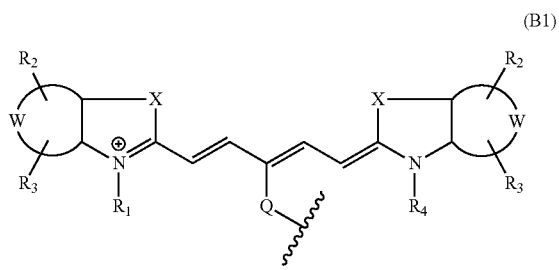

or a salt thereof, wherein:

X is independently selected from the group consisting of C(CH$_2$Y$_1$)(CH$_2$Y$_2$), O, S, and Se;

Y$_1$ and Y$_2$ are independently selected from the group consisting of H, C$_1$-C$_{20}$ aliphatic group and a C$_1$-C$_{20}$ aliphatic group substituted with —OR*, N(R*)$_2$ or —SR*;

W represents a benzo-condensed, a naphtho-condensed or a pyrido-condensed ring;

R* is alkyl;

R$_1$ is selected from the group consisting of (CH$_2$)$_x$CH$_3$, (CH$_2$)$_n$SO$_3^-$ and (CH$_2$)$_n$SO$_3$H, wherein x is an integer selected from 0 to 6 and n is an integer selected from 2 to 6;

R$_4$ is selected from the group consisting of (CH$_2$)$_x$CH$_3$, (CH$_2$)$_n$SO$_3^-$ and (CH$_2$)$_n$SO$_3$H, wherein x is an integer selected from 0 to 6 and n is an integer selected from 2 to 6;

R$_2$ and R$_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is a selected from a group consisting of a heteroaryl ring substituted with a carboxyl group or 6-membered heteroaryl ring substituted with a carbonyl group; or Q is selected from a group consisting of (i) a carboxyl functionalized heterocyclic ring, (ii) a carboxyl functionalized nitrogen containing heterocyclic ring, (iii) a carboxyl functionalized nitrogen containing 6-membered heterocyclic ring, such as pyridine, pyrimidone, pyrazine, and pyridazine, (iv) a carboxyl functionalized nitrogen containing 6-membered heterocyclic ring, such as pyridine, and (v) a carbonyl functionalized nitrogen containing 6-membered heterocyclic ring, such as pyridine.

In certain other embodiments, Formula B1 has a variable Q prepared from isonicotinic acid, nicotinic acid and picolinic acid, or a group selected from:

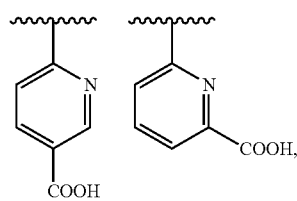

wherein, the carboxyl group is also in the form of an ester, an activated ester or carbonyl halide that is capable of reacting with nucleophiles, and can be, for example, a —C(O)-Obenzotriazolyl, —C(O)—ON-hydroxysuccinimidyl, —C(O)—O-tetrafluorophenyl, —C(O)—O-pentafluorophenyl, —C(O)—O-imidazole, and —C(O)—O-p-nitrophenyl.

In another embodiment, the fluorophore is represented by formula C:

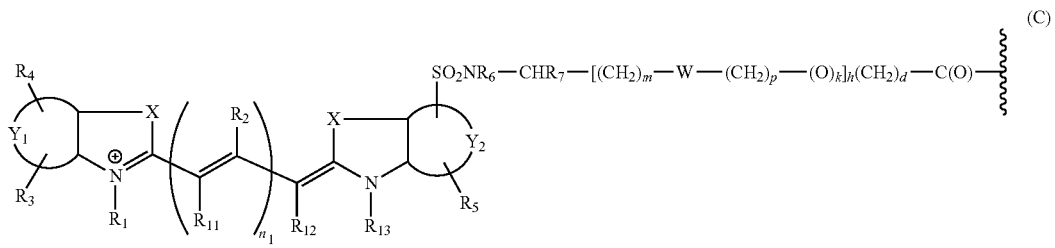

or a salt thereof, wherein:

X is independently selected from the group consisting of C(CH$_2$K$_1$)(CH$_2$K$_2$), O, S and Se;

K$_1$ and K$_2$ are independently H or C$_1$-C$_{20}$ aliphatic; or K$_1$ and K$_2$ together are part of a substituted or unsubstituted carbocyclic or heterocyclic ring;

Y$_1$ and Y$_2$ are each independently a benzo-condensed ring, a naphtha-condensed ring or a pyrido-condensed ring;

n$_1$ is 1, 2, or 3;

R$_2$, R$_{11}$ and R$_{12}$ are independently H, halogen, alkyl, alkoxy, aryloxy, aryl, a sulfonate, an iminium ion, or any two adjacent R$_{12}$ and R$_{11}$ substituents, when taken in combination, form a 4-, 5-, or 6-membered carbocyclic ring optionally substituted one or more times C$_1$-C$_6$ alkyl, halogen, or —S-alkyl;

R$_1$ and R$_{13}$ are (CH$_2$)$_x$CH$_3$, when x is an integer from 0 to 6; or R$_1$ and R$_{13}$ are independently (CH$_2$)$_n$SO$_3^-$ or (CH$_2$)$_n$SO$_3$H when n is an integer selected from 2 to 6;

R$_3$, R$_4$ and R$_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

R$_6$ is unsubstituted C1-C20 aliphatic, unsubstituted aryl, or unsubstituted alkylaryl;

R$_7$ is H, unsubstituted C1-C20 aliphatic, unsubstituted aryl, or unsubstituted alkylaryl, wherein R$_7$ is optionally substituted with halogen; or R$_6$ and R$_7$, taken together form a 4-, 5-, 6- or 7-membered heterocyclic ring optionally substituted with halogen;

W is absent or is a group selected from the group consisting of —SO$_2$NR$_6$-Q-CHR$_7$—, —O—, —C(O)O—, and —C(O)N(H)—; and h=0-70; k=0 or 1; d=0-12; m=0-12; p=0-12.

Some exemplary chemically modified fluorophores that can be used in the synthesis of the prostate specific antigen activatable agents of the invention include, for example, those listed in Table 3.

TABLE 3

| No. | Fluorophore |
|---|---|
| F1 | |
| F2 | |
| F3 | |

TABLE 3-continued

| No. | Fluorophore |
|---|---|
| F4 | |
| F5 | |
| F6 | |
| F7 | |
| F8 | |

TABLE 3-continued

| No. | Fluorophore |
|---|---|
| F9 | (structure) |
| F10 | (structure) |

In certain embodiments, two or more fluorochrome molecules can be chemically linked to the prostate specific antigen targeting moiety to produce the fluorescent prostate specific antigen agents.

In certain embodiments, one of the fluorophores may be replaced by a quencher molecule.

In the case where the imaging reporter is a fluorochrome molecule, the extinction coefficient of the prostate specific antigen activatable agents can be calculated as the ratio of the absorbance of dye at its absorption maxima (for example at ~670 nm for VivoTag 680) in a 1 cm path length cell to the concentration of particles using the formula $\epsilon=A/cl$, where A is absorbance, c is molar concentration and l is path length in cm.

Fluorescent silicon nanoparticles may also have the following properties: (1) high quantum yield (i.e., quantum yield greater than 5% in aqueous medium), (2) narrow emission spectrum (i.e., less than 75 nm; more preferably less than 50 nm), (3) spectrally separated absorption and emission spectra (i.e., separated by more than 20 nm; more preferably by more than 50 nm), (3) have high chemical stability and photostability (i.e., retain luminescent properties after exposure to light), (4) are biocompatible (see below) or can be made more biocompatible; (5) are non toxic or minimally toxic to cells or subjects at doses used for imaging protocols, (as measured for example, by $LD_{50}$ or irritation studies, or other similar methods known in the art) and/or (6) have commercial viability and scalable production for large quantities (i.e., gram and kilogram quantities) required for in vivo and human use.

Other exemplary fluorophores include metal oxide nanoparticles that are fluorescent and can be used in a variety of in vitro and vivo applications. In one embodiment, the prostate specific antigen targeting moiety is conjugated to fluorescent metal oxide nanoparticles with one or more of the following features: (1) a polymer coating suitable for attaching a plurality of fluorochromes thereby achieving large extinction coefficients (in excess of 1,000,000 $M^{-1}$ $cm^{-1}$), (2) a non-crosslinked polymer coating suitable for attaching from about 10 to about 300 fluorochromes per particle, (3) a polymer coating suitable for attaching a plurality of fluorochromes in a manner that does not significantly compromise the quantum yield of the fluorochromes (e.g., the nanoparticles retain at least 50% of the fluorescent signal that is created by substantially the same number of free fluorochromes when tested under the same conditions), and (4) a polymer coating that is amenable to efficient chemical linking of biomolecules with retention of their biological properties to yield molecular imaging agents. The fluorescent metal oxide nanoparticles are highly stable molecular imaging agents in vitro, both before and after chemical linking of fluorochromes and bacterium targeting agents, but yet are labile and/or degradable in vivo.

Furthermore, the prostate specific antigen targeting moiety can be conjugated to molecules capable of eliciting photodynamic therapy. These include, but are not limited to, Photofrin, Lutrin, Antrin, aminolevulinic acid, hypericin, benzoporphyrin derivative, and select porphyrins.

In certain embodiments, the imaging agents are incorporated on a nanoparticle with one or more of the following features: (1) a polymer coating suitable for attaching a plurality of agents (2) a non-crosslinked polymer coating suitable for attaching from about 10 to about 300 agents per particle, and (3) a polymer coating that is amenable to efficient chemical linking of the agents with retention of their biological properties to yield molecular imaging agents. The agent modified metal oxide nanoparticle can be a highly stable molecular imaging agent in vitro, both before and after chemical linking of the agents, but yet are labile and/or degradable in vivo.

It is appreciated that the prostate specific antigen activatable agent conjugated metal oxide nanoparticles can be formulated into a pharmaceutical composition suitable for administration to a subject, for example, an animal and/or a human subject.

(iii) Ultrasound Reporters

For ultrasound imaging, the imaging reporter can include gas-filled bubbles such as Levovist, Albunex, or Echovist, or particles or metal chelates where the metal ions have atomic numbers 21-29, 42, 44 or 57-83. Examples of such compounds are described in Tyler et al., Ultrasonic Imaging, 3, pp. 323-29 (1981) and D. P. Swanson, "Enhancement Agents for Ultrasound: Fundamentals," Pharmaceuticals in Medical Imaging, pp. 682-87 (1990).

(iv) X-Ray Reporters

Exemplary reporters can comprise iodinated organic molecules or chelates of heavy metal ions of atomic numbers 57 to 83. Examples of such compounds are described in M. Sovak, ed., "Radiocontrast Agents," Springer-Verlag, pp. 23-125 (1984) and U.S. Pat. No. 4,647,447.

C. Linkers

Linker or spacer moieties (L) can be used to chemically link one or more chemical modifiers (M) to the fluorophore and/or to link the prostate specific antigen targeting moiety to Q or, if Q is absent, directly to the fluorophores of the agents of the present invention. Useful linker moieties include both natural and non-natural amino acids and nucleic acids, peptides, such as glycine, β-alanine, γ-aminobutyric acid or aminocaproic acid, as well as synthetic linker molecules such as aminoethyl maleimide or aminomethyl benzoic acid, or a polymer such as homobifunctional or heterobifunctional polyethylene glycol (PEG). When the linker is a peptide, the peptide optionally may include proteolytic cleavage site that can be cleaved with a variety of agents, for example, an enzyme.

It is understood that there is no particular structural, size or content limitation for a given linker. Linkers can include, for example, a variety of functional groups such as maleimide, dithiopyridyl, thiol, azide, alkene, or alkyne that permit the assembly of molecules of diverse architecture.

Linkers can be homofunctional linkers or heterofunctional linkers. For example, amine ($NH_2$)-functionalized moieties can be reacted with bifunctional cross-linkers designed to react with amino groups. Particularly useful conjugation reagents that can facilitate formation of a linker or facilitate covalent linkage between, for example, a fluorophore, and an enzymatically cleavable oligopeptide can include a N-hydroxysuccinimide (NHS) ester and/or a maleimide. The NHS ester can react with the amine group of, for example, a peptide or fluorophore. The maleimide can react with the sulfhydryl group of another molecule. Other particularly useful linker moieties are bifunctional crosslinkers such as N-succinimidyl 3-(2-pyridyldithio)propionate (SPDP), long chain-SPDP, maleimidobenzoic acid-N-hydroxysuccinimide ester (MBS), succinimidyl trans-4-(maleimidylmethyl)cyclohexane-1-carboxylate (SMCC), succinimidyl iodoacetate (SIA).

In certain embodiments a linker, if present, may be a derivative of a diamine. A diamine moiety or derivative can provide a linker arm of varying lengths and chemistries for chemically linking molecules by derivatizing, optionally, with carboxylic acids. Non-limiting examples of diamines include ethylenediamine (EDA), propylenediamine, spermidine, spermene, hexanediamine, and diamine-amino acids, such as homolysine, lysine, ornithine, diaminobutyric acid and diaminopropionic acid. In other embodiments, moieties of an imaging agent can be chemically linked to a dicarboxylic acid, for example, succinic acid, glutaric acid, suberic acid, or adipic acid. In one embodiment, the linker is aminoethylmaleimide.

In certain embodiments, a linker can be branched, for example glutamic acid or 5-(aminomethyl)isophthalic acid, or a dendrimer, such as a lysine or glutamic acid dendrimer, with multiple M groups linked to a single site on the fluorophore.

In certain embodiments, L is a functionalized, substituted or unsubstituted $C_1$-$C_{18}$ alkyl, alkenyl, alkynyl, alkoxy, or thioalkyl group. In other embodiments, L is functionalized, substituted or unsubstituted aromatic or heteroaromatic ring. In other embodiments, L is absent.

In certain embodiments, a linker can be formed from an azide moiety that can react with substituted alkynes in an azide-acetylene Huisgen [3+2] cycloaddition. In certain embodiments the azide or alkyne linker can link a polyethyleneglycol (PEG) moiety to, for example, an enzymatically cleavable oligopeptide. Other contemplated linkers include propargylglycine, pentanoyl, pentynoic acid, propargylic acid, and/or propargylamine moieties.

In certain embodiments, the imaging reporters are directly chemically linked to the prostate specific antigen targeting moiety using reactive NHS esters groups on the F which react with the amine group of the amino-functionalized prostate specific antigen targeting moiety. In certain other embodiments, carboxylic acid groups on the F can be activated in situ by activating agents known in the art, such as 2-(1H-benzotriazole-1-yl)-1,1,3,3,-tetramethyluronium hexafluorophosphate (HBTU), 1-ethyl-3-(3'-dimethylaminopropyl)-carbodiimide hydrochloride (EDC), N,N'-dicyclohexylcarbodiimide (DCC), N,N'-disuccinimidyl carbonate (DSC). In other embodiments, Fs containing a sulfhydryl or thiol group, can be chemically linked to the prostate specific antigen targeting moiety via a bifunctional cross-linker that has a second moiety that can react with a sulfhydryl (thiol) group. Such crosslinking agents include, for example and as described above, SPDP, long chain-SPDP, SIA, MBS, SMCC, and others that are well known in the art.

Useful linker moieties include both natural and non-natural amino acids, oligopeptides, for example, linear or cyclic oligopeptides, and nucleic acids. The linker can be a peptide or peptide moiety. The linker can optionally include a proteolytic or non-proteolytic cleavage site, such as an ester linkage, that can be cleaved due to pH changes at the site of interest.

The term "amino acid" as used herein is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3',5,5'-tetraiodothyronine.

Modified or unusual amino acids which can be used to practice the invention include, but are not limited to, D-amino acids, hydroxylysine, dehydroalanine, pyrrolysine, 2-aminoisobutyric acid, gamma aminobutyric acid, 5-hydroxytryptophan, S-adenosyl methionine, S-adenosyl homocysteine, 4-hydroxyproline, an N-Cbz-protected amino acid, 2,4-diaminobutyric acid, homoarginine, norleucine, N-methylaminobutyric acid, naphthylalanine, phenylglycine, .beta.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, a "pseudopeptide" or "peptidomimetic" is a compound which mimics the structure of an amino acid residue or a peptide, for example, by using linking groups other than via amide linkages (pseudopeptide bonds) and/or by using non-amino acid substituents and/or a modified amino acid residue. A "pseudopeptide residue" means that portion of a pseudopeptide or peptidomimetic that is present in a peptide. The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation. The following conventional three-letter amino acid abbreviations are used herein: Ala=alanine; Aca=aminocaproic acid, Ahx=6-aminohexanoic acid, Arg=arginine; Asn=asparagines; Asp=aspartic acid; Cha=cyclohexylalanine; Cit=citrulline; Cys=cysteine; Dap=dianiinopropionic acid; Gin=glutamine; Glu=glutamic acid; Gly=glycine; His=histidine; Ile=isoleucine; Leu=leucine; Lys=lysine; Met=methionine; Nal=naphthylalanine; Nle=norleucine Orn=ornithine; Phe=phenylalanine; Phg=phenylglycine; Pro=praline; Sar=sarcosine; Ser=serine; Thi=Thienylalanine; Thr=threonine; Trp=tryptophan; Tyr=tyrosine; and Val=valine; Hyp=hydroxyproline; Cha=cyclohexylalanine; Chg=cyclohexylglycine. Use of the prefix D-indicates the D-isomer of that amino acid; for example D-lysine is represented as D-Lys.

The peptides can be synthesized using either solution phase chemistry or solid phase chemistry or a combination of both (Albericio, Curr. Opinion. Cell Biol., 8, 211-221 (2004), M. Bodansky, Peptide Chemistry: A Practical Textbook, Springer-Verlag; N. L. Benoiton, Chemistry of Peptide Synthesis, 2005, CRC Press).

Selective or orthogonal amine protecting groups may be required to prepare the agents of the invention. As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Synthesis, Biology, Vol. 3, Academic Press, New York (1981). Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, benzoylbenzoyl.

In certain embodiments the enzymatically cleavable oligopeptide can include oligo-L-arginine, oligo-L-lysine, oligo-L-aspartic acid or oligo-L-glutamic acid.

The enzymatically cleavable oligopeptide of the linker is cleavable by at least one enzyme chosen from hydrolases, elastases, cathepsins, matrix metalloproteases, peptidases, exopeptidases, endopeptidases, carboxypeptidases, glycosidases, lipases, nucleases, lyases, amylases, phospholipases, phosphatases, phosphodiesterases, sulfatases, serine proteases, subtilisin, chymotrypsin, trypsin, threonine proteases, cysteine proteases, calpains, papains, caspases, aspartic acid proteases, pepsins, chymosins, glutamic acid proteases, renin, reductases, and parasitic, viral and bacterial enzymes.

D. Chemical Modifiers

Depending upon the intended use, the prostate specific antigen activatable agents can comprise one or more chemical modifiers (M), which can alter the physical, chemical or biological properties of the prostate specific antigen activatable agent. In particular, a plurality of Ms can be chemically linked to the fluorophore moiety of the agent. The Ms can be the same or can be different for each occurrence. For example, the Ms may render the prostate specific antigen activatable agents more useful for biological imaging, that is, for example, more water soluble, or more dispersible in media for administration, with increased binding specificity, or less immunogenic, or less toxic, or with reduced non-specific binding, altered biodistribution and pharmacokinetic compared to an unsubstituted or lesser substituted fluorophore moiety.

For example, incorporation of methoxypolyethylene glycol (mPEG) or polypeptides or a plurality of anionic Ms may function to modify the pharmacodynamics and blood clearance rates of the prostate specific antigen activatable agents in vivo. Other Ms can be chosen to accelerate the clearance of the prostate specific antigen activatable agents from background tissue, such as muscle or liver, and/or from the blood, thereby reducing the background interference and improving image quality. Additionally, the Ms can be used to favor a particular route of excretion, e.g., via the kidneys rather than via the liver. The Ms can also aid in formulating probes in pharmaceutical compositions or may be used to alter or preserve the signal reporting properties of the prostate specific antigen activatable agents. In particular, chemical linking of polyethylene glycol (PEG) or a derivative thereof to prostate specific antigen activatable agents can result in longer blood residence time (longer circulation) and decreasing immunogenicity.

Exemplary modifiers include polyethylene glycol (PEG) and derivatives thereof (for example, alkoxy polyethylene glycol (for example, methoxypolyethylene glycol, ethoxypolyethylene glycol and the like), branched polypropylene glycol, polypropylene glycol, a graft copolymer of polylysine and methoxypolyethyleneglycol, amino acids, peptides, lipids, fatty acids, palmitate, phospholipids, phospholipid-PEG conjugates, carbohydrates (such as dextran, amino-dextran, carboxymethyl-dextran), iron oxide nanoparticles, sulfonates, polysulfonates, cysteic acid, naphthylalanine, phenylalanine, and 3,3-diphenylpropylamine taurine, phosphonates, phosphates, carboxylates and polycarboxylates.

In certain embodiments, the chemical modifier M is an anionic moiety selected from the group consisting of carboxylate, phosphonate, phosphate, iminodiacetate, cysteic acid, or taurine.

In certain embodiments, the chemical modifier M is a sulfonate or polysulfonate.

In certain embodiments, the chemical modifier M is a hydrogen, alcohol, sulfonamide, sulfoxide, sulfone, ketone, an amino acid such as glutamic acid or taurine, a polyamino acid such as polycysteic acid, oligo- or polyethylene glycol, an amine, a quaternary ammonium ion, or a carbohydrate such as glucosamine, galactosamine or mannosamine.

In certain embodiments, the chemical modifier M is a metal chelator, such as ethylenediamine tetraacetic acid (EDTA), diethylenetriamine pentaacetic acid (DTPA), or tetraazacyclododecane tetraacetic acid (DOTA). In another aspect of the invention, one or more metal chelating M groups are coordinated to a metal ion.

In certain embodiments, as discussed above, the biological modifier may be a PEG moiety that has a molecular weight, for example, from about 0.1 kDa to about 50 kDa, about 5 kDa to about 45 kDa, or about 10 kDa to about 40 kDa. Alternatively, the PEG may be dPEG, functionalized at a discrete molecular weight, for example, of about 1100 daltons.

In certain embodiments, the PEG is methoxyPEG$_{(5000)}$-succinimidylpropionate (mPEG-SPA), methoxyPEG$_{(5000)}$-succinimidylsuccinate (mPEG-SS). Such PEGS are commercially available from Nektar Therapeutics or SunBiowest or LaysanBio or NOF.

The PEG moiety can be conjugated to reactive amines on the prostate specific antigen activatable agent via a carboxyl functionality. Alternatively, the PEG modifier can be conjugated to the prostate specific antigen activatable agent by using a thiol reactive cross linker and then reacting with a thiol group on the PEG. Alternatively, the PEG moiety can be conjugated to reactive carboxylic acid on the prostate specific antigen activatable agent via an amide functionality.

In one embodiment, the PEG may be branched, or Y-shaped, as available from JenKem USA or NOF, or comb-shaped, or synthesized by coupling two or more PEGs to a small molecule such as glutamic acid.

In other embodiments, the biological modifier can be polyvinylpyrrolidone (PVP)-type polymers. The biological modifier can be a functionalized polyvinylpyrrolidone, for example, carboxy or amine functionalized on one (or both) ends of the polymer (as available from Polymersource) or within the polymer chain.

Alternatively, the biological modifier can include Poly N-(2-hydroxypropyl)methacrylamide (HPMA), or functionalized HPMA (amine, carboxy, etc.), Poly(N-isopropyl acrylamide) or functionalized poly(N-isopropylacrylamide).

Biological modifiers can include straight or branched chain acyl groups, such as pentynoyl; acidic groups, such as succinyl; lower alkyl groups, such as methyl, ethyl, propyl, etc.; carboxyalkyl groups, such as carboxyethyl; haloalkyl groups, such as trifluoromethyl; and the like.

In general, the chemical linking of Ms does not adversely affect the affinity and/or binding properties of the prostate specific antigen activatable agents.

E. First Group of Exemplary Prostate Specific Antigen Activatable Agents

The prostate specific antigen targeting moieties, imaging reporters, linkers, and optionally chemical modifying moieties described above can be combined in different permutations to provide a variety of prostate specific antigen activatable agents.

Accordingly, one aspect of the invention provides a prostate specific antigen activatable agent that comprises one prostate specific antigen targeting moiety chemically linked to two fluorophores, wherein a plurality of chemical modifying moieties (M) is chemically linked to the fluorophore. Optionally, one or more linker (L) moieties can be used to chemically link the prostate specific antigen targeting moiety to the fluorophore or the M to the fluorophore.

In certain embodiments, the prostate specific antigen activatable agent will have an affinity for enzymatically active prostate specific antigen. In other embodiments, the affinity for enzymatically active prostate specific antigen is greater than enzymatically inactive prostate specific antigen. A "prostate specific antigen targeting moiety", as defined herein, is a molecule that specifically binds with the mature prostate specific antigen that is enzymatically active.

The "fluorophore" may be any suitable chemical or substance which is used to provide fluorescent signal or contrast in imaging and that is detectable by imaging techniques. In certain embodiments, fluorophore comprises, for example, a cyanine dye, carbocyanine dye, indocyanine dye, or a polymethine fluorescent dye. In certain embodiments, fluorophore comprises a symmetrical cyanine dye. In other embodiments, fluorophore comprises and unsymmetrical cyanine dye. In other embodiments, fluorophore may also be modified with a plurality of chemical modifying groups allowing optimization of the in vitro and in vivo properties of the agent and ultimately the performance of the agent as a fluorescence imaging agent.

The prostate specific antigen activatable agent can have an affinity for enzymatically active prostate specific antigen. In certain embodiments, the prostate specific antigen activatable agent binds to the mature enzymatically active prostate specific antigen that is elevated in serum during the pathology of prostate cancer.

Another aspect of the invention provides prostate specific antigen activatable agent comprising:

(i) a prostate specific antigen targeting moiety comprising an enzymatically cleavable oligopeptide sequence; and (ii) two or more imaging reporters chemically linked, optionally through a linker (L) moiety, to the prostate specific antigen targeting moiety; and (iii) one or two optional chemical modifying moiety M chemically linked to the prostate specific antigen targeting moiety.

The term "chemically linked" is understood to mean connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions.

Another aspect of the invention provides a prostate specific antigen agent comprising:

(i) a prostate specific antigen targeting moiety comprising an enzymatically cleavable oligopeptide sequence;

(ii) an imaging reporter chemically linked, optionally through a linker (L) moiety, to the prostate specific antigen targeting moiety; and (iii) a fluorescent reporter chemically linked, optionally through a linker (L) moiety, to the prostate specific targeting activatable moiety wherein the fluorescent moiety bears a plurality of chemical modifying groups.

F. Second Group of Exemplary Prostate Specific Antigen Activatable Agents

Another aspect of the invention provides a compound of formula (I):

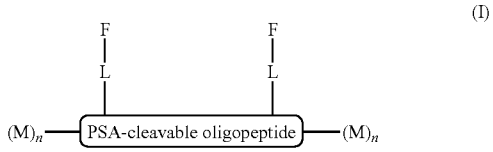

or a salt thereof, wherein:

F represents independently for each occurrence a fluorochrome or a quencher;

L represents independently for each occurrence a bond or a linker; and

M is a modifier, attached to either the C or N terminus, or both, of the oligopeptide; and n represents independently 0 or 1, providing that there is at least one occurrence of M.

In certain embodiments, the agent is fluorescent in the far-red or near-infrared wavelengths.

In certain embodiments, the chemical modifying moiety (M) is selected from the group consisting of a hydrogen, alcohol, sulfonate, polysulfonate, cysteic acid, sulfonamide, sulfoxide, sulfone, carboxylate, ketone, phosphonate, phosphate; iminodiacetate, ethylenediamine tetraacetic acid, diethylenetriamine pentaacetic acid, tetraazacyclododecane tetraacetic acid, an amino acid or polyamino acid, oligo- or polyethylene glycol, amine, quaternary ammonium ion, sugars, glucosamine, galactosamine, mannosamine, polyethylene glycol (PEG) and derivatives thereof, for example, alkoxy polyethylene glycol (for example, methoxypolyethylene glycol, ethoxypolyethylene glycol and the like), branched polypropylene glycol, polypropylene glycol, a graft copolymer of poly-lysine and methoxypolyethyleneglycol, peptides, lipids, fatty acids, palmitate, phospholipids, phospholipid-PEG conjugates, carbohydrates (such as dextran, amino-dextran, carboxymethyl-dextran), iron oxide nanoparticles, naphthylalanine, phenylalanine, 3,3-diphenylpropylamine, taurine, phosphonates, phosphates, carboxylates and polycarboxylates.

In certain embodiments, the chemical modifying moiety (M) is hydrogen, sulfonate, polysulfonate, sulfonamide, sulfoxide, sulfone, carboxylate, ketone, phosphonate, phosphate, iminodiacetate, or a radical of: an alcohol, cysteic acid, an amine, ethylenediamine tetraacetic acid, diethylenetriamine pentaacetic acid, tetraazacyclododecane tetraacetic acid, an amino acid or polyamino acid, oligo- or polyethylene glycol, quaternary ammonium ion, a sugar, glucosamine, galactosamine, mannosamine, polyethylene glycol (PEG) and derivatives thereof, branched polypropylene glycol, polypropylene glycol, a graft copolymer of poly-lysine and methoxypolyethyleneglycol, a peptide, a lipid, a fatty acid, palmitate, a phospholipid, a phospholipid-PEG conjugate, a carbohydrate, polyvinylpyrrolidone, an iron oxide nanoparticle, naphthylalanine, phenylalanine, 3,3-diphenylpropylamine, taurine, a phosphonate, a phosphate, a carboxylate, or a polycarboxylate.

In other embodiments, the chemical modifier(s) M reduce the nonspecific cell membrane permeability of the agent. In other embodiments, the chemical modifier(s) M reduce the nonspecific tissue accumulation of the agent when administered to a live animal.

In certain embodiments, the bond or linker moiety (L) comprises a diradical of a moiety selected from the group consisting of glycine, alanine, β-alanine, —NH—$(CH_2)_n$—C(=O)—where n=1-8, 4-aminomethylbenzoic acid, cysteic acid, glutamic acid, amino-polyethylene glycol-carboxylic acid, amino-polyethylene glycol amine, ethylenediamine, propylenediamine, spermidine, spermine, hexanediamine, and diamine-amino acids, such as homolysine, lysine, ornithine, diaminobutyric acid and diaminopropionic acid, succinic acid, glutaric acid, suberic acid, adipic acid, amide, triazole, urea, or thiourea.

G. Third Group of Exemplary Prostate Specific Antigen Activatable Agents

Another aspect of the invention provides a prostate specific antigen (PSA) activatable agent represented by Formula II:

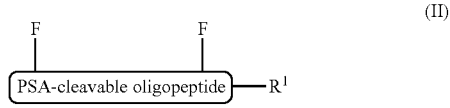

or a salt thereof, wherein:

$R^1$ is hydrogen, —($C_{1-6}$ alkylene)-methoxypolyethylene glycol, or —($C_{1-6}$ alkylene)-N(R*)C(O)—($C_{1-6}$ alkylene)-N(—($C_{1-6}$ alkylene)-methoxypolyethylene glycol)C(O)—($C_{1-6}$ alkylene)-methoxypolyethylene glycol;

R* is hydrogen or unsubstituted $C_{1-6}$ alkyl;

F represents independently for each occurrence structural Formula IIa or IIb:

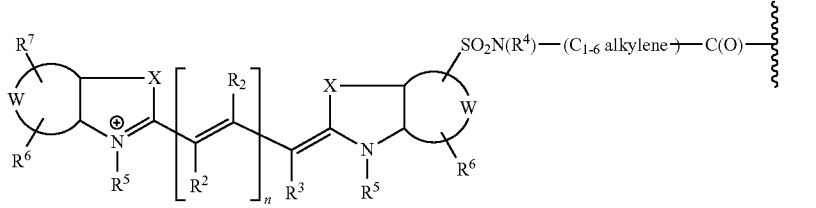

wherein:

$R^2$ represents independently for each occurrence hydrogen or unsubstituted $C_{1-6}$ alkyl, or two adjacent occurrences of $R^2$ are taken together with the atoms to which they are attached to form a 5- or 6-membered carbocyclic ring;

$R^3$ is hydrogen or unsubstituted $C_{1-6}$ alkyl, or $R_3$ and an adjacent occurrence of $R^2$ are taken together with the atoms to which they are attached to form a 5- or 6-membered carbocyclic ring;

$R^4$ is hydrogen or unsubstituted $C_{1-6}$ alkyl;

$R^5$ represents independently for each occurrence unsubstituted $C_{1-6}$ alkyl, unsubstituted $C_{1-6}$ alkyl-$SO_3^-M^+$, or unsubstituted $C_{1-6}$ alkyl-$SO_3H$;

$R^6$ and $R^7$ each represent independently for each occurrence occurrence hydrogen, —$SO_3H$, or —$SO_3^-M^+$;

M is a monovalent cation or absent;

n is 1, 2, or 3;

W represents a benzo-condensed, a naphtho-condensed, or a pyrido-condensed ring;

X represents independently for each occurrence $C(CH_2Y_1)(CH_2Y_2)$, O, or S; and $Y_1$ and $Y_2$ are independently hydrogen or unsubstituted $C_{1-6}$ alkyl; and Formula IIb is represented by:

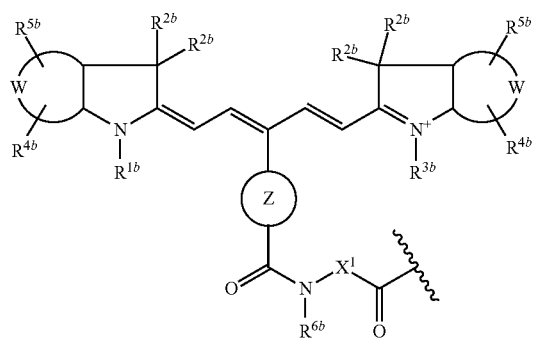

(IIb)

wherein:

$R^{1b}$ and $R^{3b}$ each represent independently unsubstituted $C_{1-6}$ alkyl, unsubstituted $C_{1-6}$ alkyl-$SO_3^-M^+$, or unsubstituted $C_{1-6}$ alkyl-$SO_3H$;

$R^{2b}$ each represents independently for each occurrence methyl, ethyl, or propyl;

$R^{4b}$ and $R^{5b}$ each represent independently for each occurrence occurrence hydrogen, —$SO_3H$, or —$SO_3^-M^+$;

$R^{6b}$ is hydrogen or $C_{1-6}$ unsubstituted alkyl;

M is a monovalent cation or absent;

W represents a benzo-condensed, a naphtho-condensed, or a pyrido-condensed ring;

Z is arylene;

$X^1$ is unsubstituted $C_{1-8}$ alkylene; and the PSA-cleavable oligopeptide is one of the following:

(SEQ ID NO: 14)

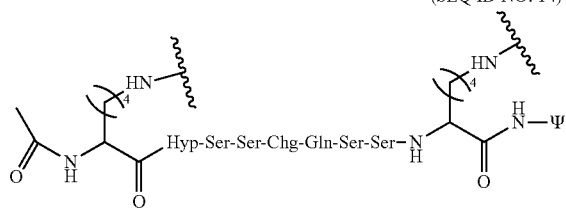

(SEQ ID NO: 15)

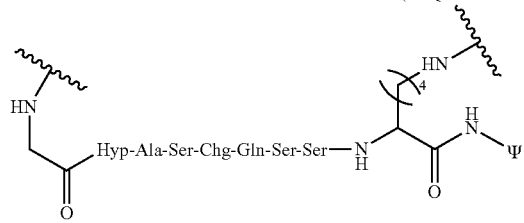

(SEQ ID NO: 16)

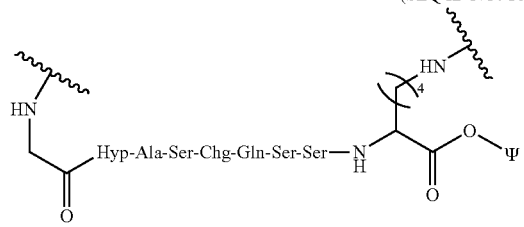

(SEQ ID NO: 17)

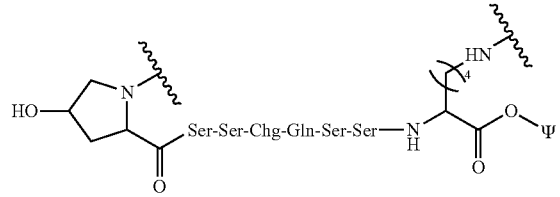

(SEQ ID NO: 18)

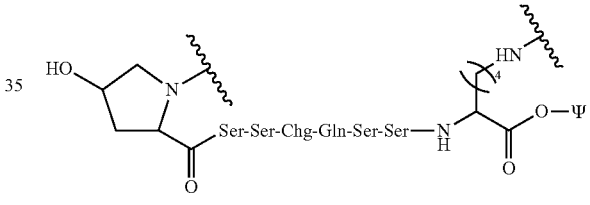

(SEQ ID NO: 19)

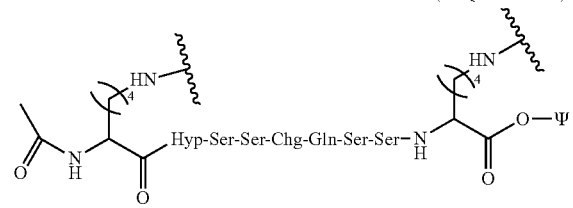

(SEQ ID NO: 20)

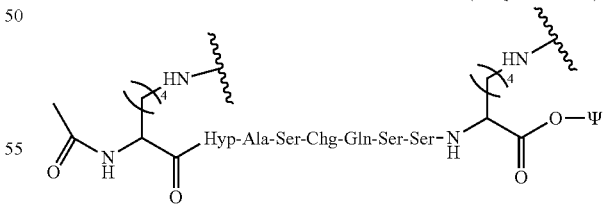

(SEQ ID NO: 21)

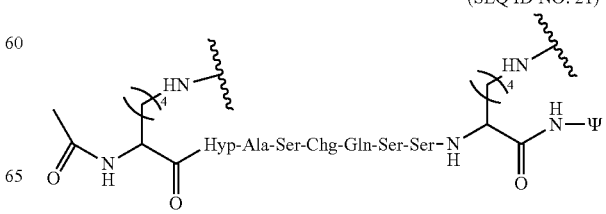

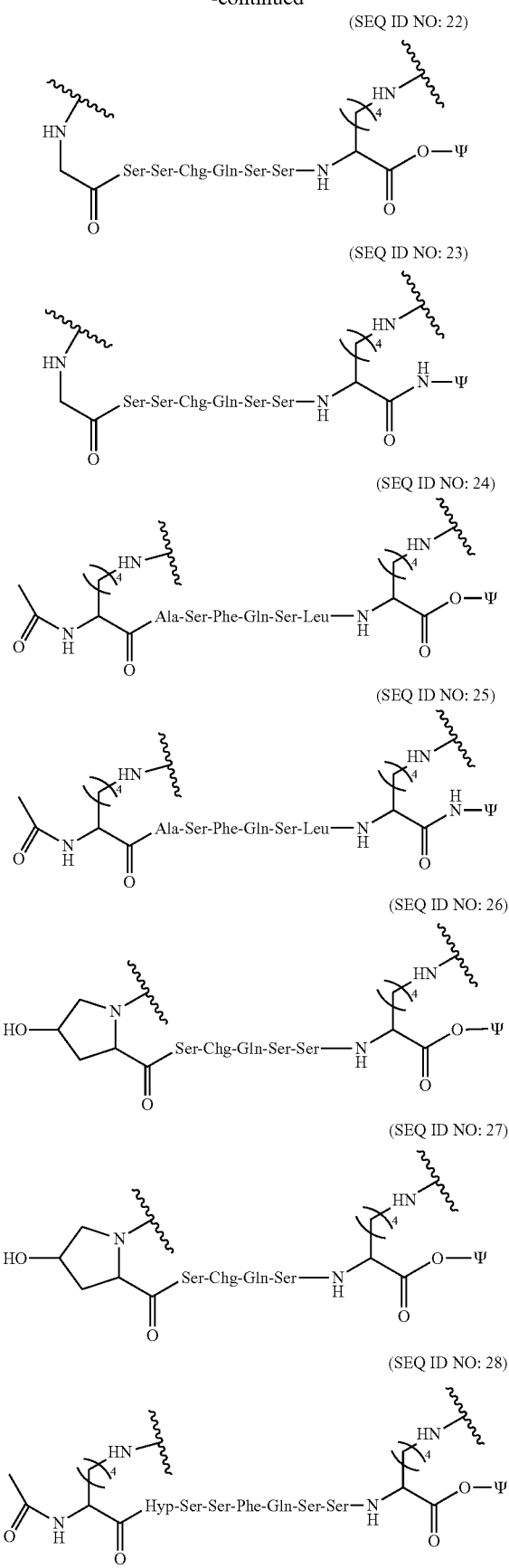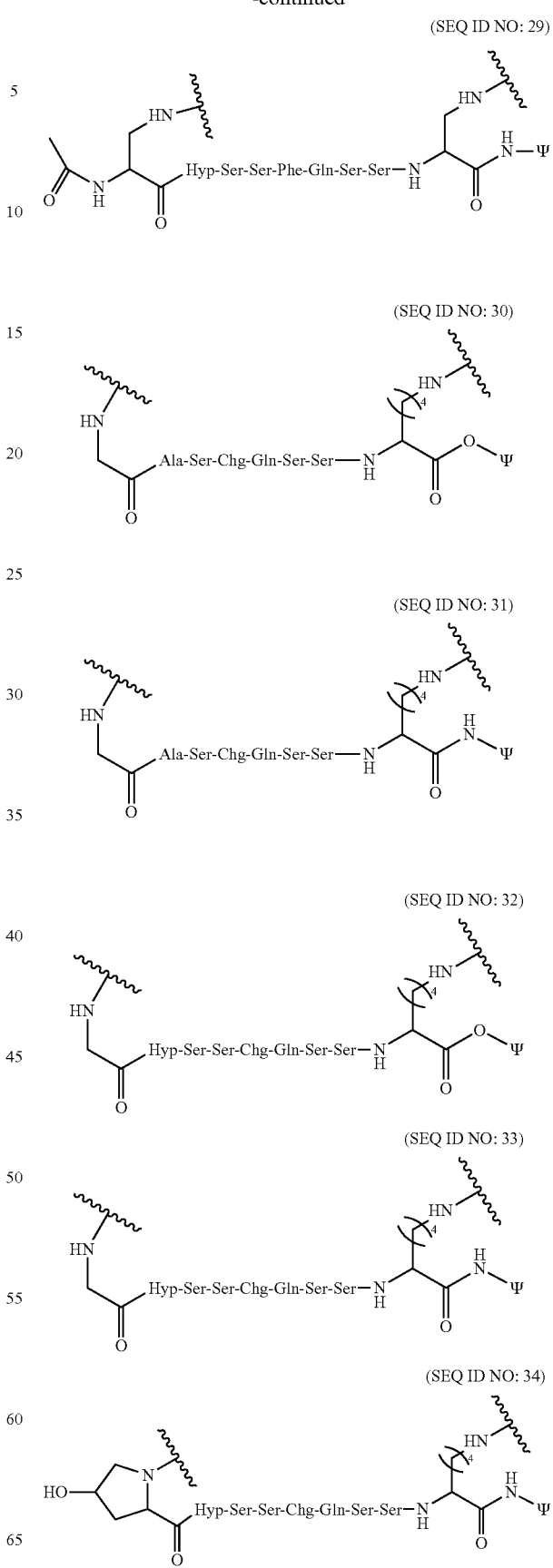

-continued

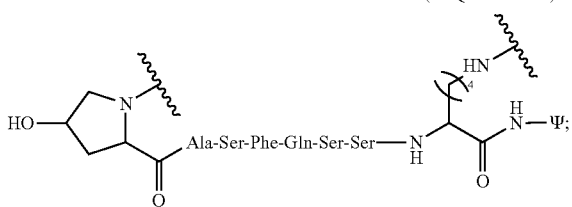

(SEQ ID NO: 35)

where ψ is a covalent bond to $R^1$.

In certain embodiments, F is represented by structural Formula IIa. In certain embodiments, W represents a benzo-condensed ring. In certain embodiments, $R^6$ and $R^7$ each represent independently for each occurrence occurrence hydrogen or —$SO_3H$.

In certain embodiments, F is represented by the following structural formula:

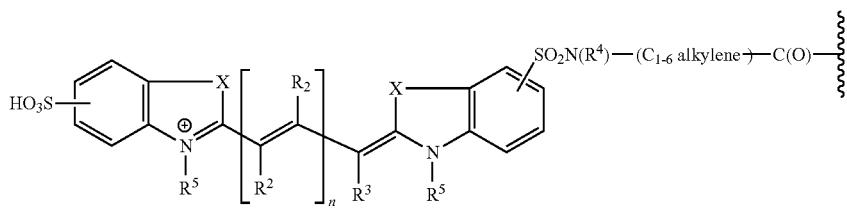

wherein:

R² represents independently for each occurrence hydrogen or unsubstituted $C_{1-6}$ alkyl, or two adjacent occurrences of $R^2$ are taken together with the atoms to which they are attached to form a 5- or 6-membered carbocylic ring;

$R^3$ is hydrogen or unsubstituted $C_{1-6}$ alkyl, or $R_3$ and an adjacent occurrence of $R^2$ are taken together with the atoms to which they are attached to form a 5- or 6-membered carbocylic ring;

$R^4$ is hydrogen or unsubstituted $C_{1-6}$ alkyl;

$R^5$ represents independently for each occurrence unsubstituted $C_{1-6}$ alkyl-$SO_3^-M^+$ or unsubstituted $C_{1-6}$ alkyl-$SO_3H$;

M is a monovalent cation or absent;

n is 1, 2, or 3; and

X is $C(CH_3)_2$ or $C(CH_2CH_3)_2$.

In certain embodiments, $R^2$ and $R^3$ are hydrogen. In certain embodiments, $R^4$ is methyl. In certain embodiments, n is 2 or 3. In certain embodiments, X is $C(CH_3)_2$. In certain embodiments, F is represented by one of the following structural formulae:

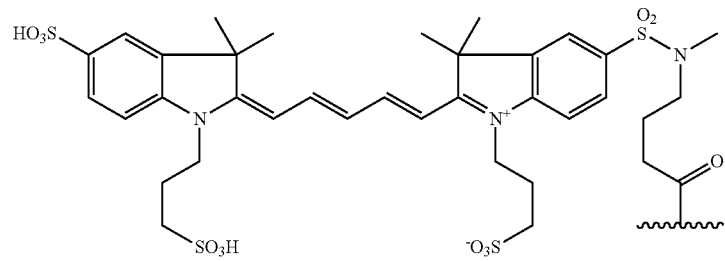

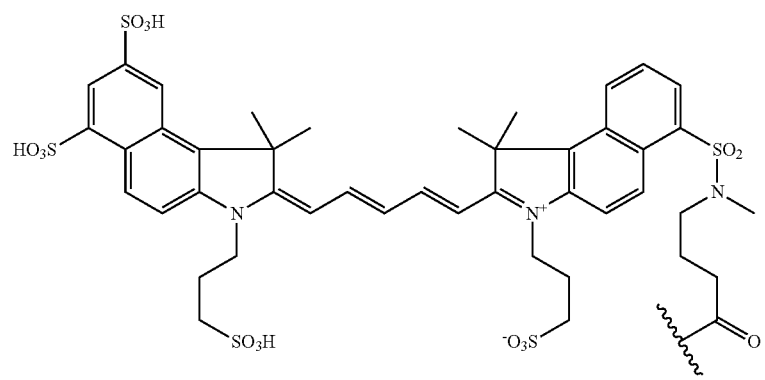

-continued

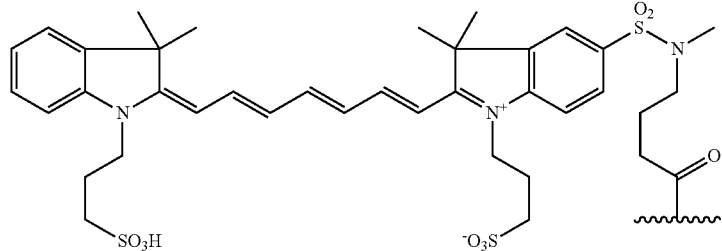

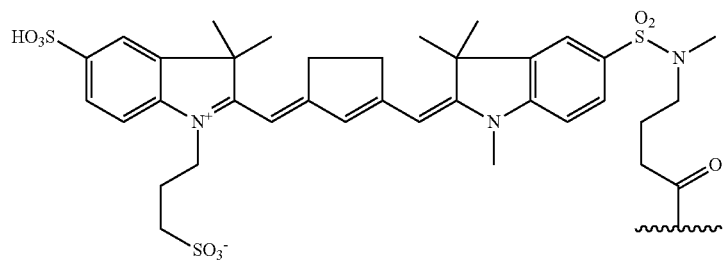

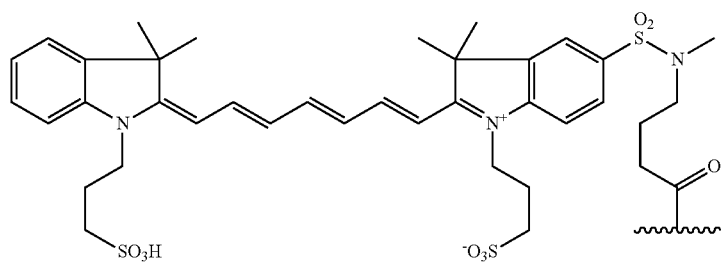

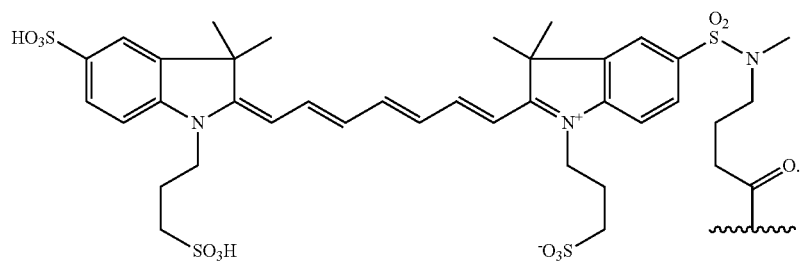

In certain other embodiments, F is represented by structural Formula IIb. In certain embodiments, W represents a benzo-condensed ring. In certain embodiments $R^{4b}$ and $R^{5b}$) each represent independently for each occurrence occurrence hydrogen or —$SO_3H$.

In certain embodiments, F is represented by the following structural Formula:

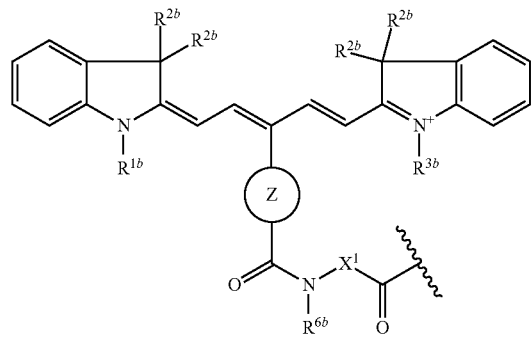

wherein:

$R^{1b}$ and $R^{3b}$ each represent independently unsubstituted $C_{1-6}$ alkyl, unsubstituted $C_{1-6}$ alkyl-$SO_3^-M^+$, or unsubstituted $C_{1-6}$ alkyl-$SO_3H$;

$R^{2b}$ represents independently for each occurrence methyl or ethyl;

$R^{6b}$ is hydrogen or methyl;

M is a monovalent cation or absent;

Z is arylene; and $X^1$ is unsubstituted $C_{1-6}$ alkylene.

In certain embodiments, $R^{1b}$ and $R^{3b}$ each represent independently unsubstituted $C_{1-6}$ alkyl-$SO_3^-M^+$ or unsubstituted $C_{1-6}$ alkyl-$SO_3H$. In certain embodiments, $R^{2b}$ is methyl. In certain embodiments, $R^{6b}$ is hydrogen. In certain embodiments, Z is a 6-membered heteroaromatic diradical. In certain embodiments, Z is

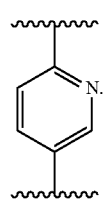

In certain embodiments, $X^1$ is —(CH$_2$)$_4$—, —(CH$_2$)$_5$—, or —(CH$_2$)$_6$—. In certain embodiments, F is represented by one of the following structural formulae:

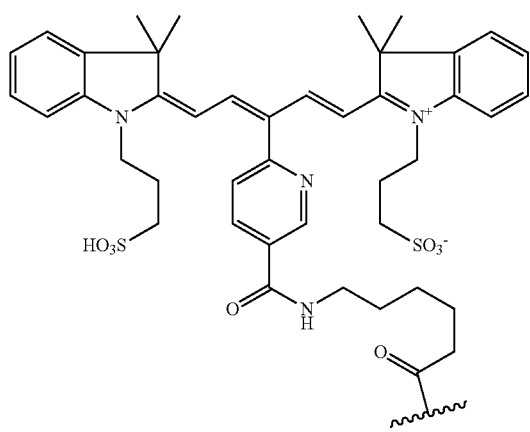

In certain embodiments, the PSA-cleavable oligopeptide is one of the following:

(SEQ ID NO: 14)
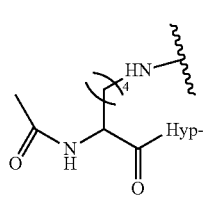

(SEQ ID NO: 15)
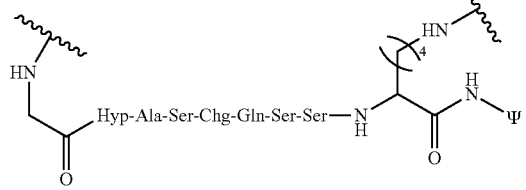

(SEQ ID NO: 17)
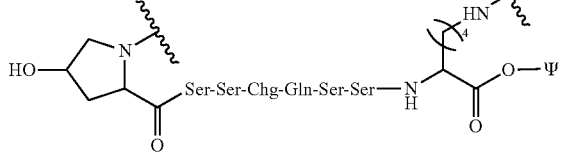

(SEQ ID NO: 33)
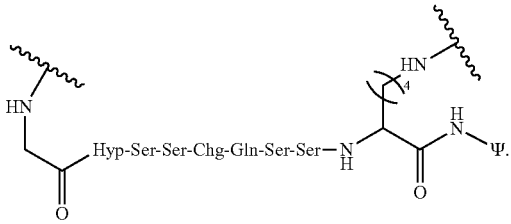

In certain embodiments, $R^1$ is —(C$_{1-6}$ alkylene)-N(M)C(O)—(C$_{1-6}$ alkylene)-N(—(C$_{1-6}$ alkylene)-methoxypolyethylene glycol))C(O)—(C$_{1-6}$alkylene)-methoxypolyethylene glycol. In certain embodiments, $R^1$ is In certain embodiments, the methoxypolyethylene glycol has a weight average molecular weight of about 5,000 g/mol to about 30,000 g/mol. In certain embodiments, the methoxypolyethylene glycol has a weight average molecular weight of about 20,000 g/mol.

In certain other embodiments, $R^1$ is hydrogen.

Another aspect of the invention provides a prostate specific antigen (PSA) activatable agent represented by Formula III:

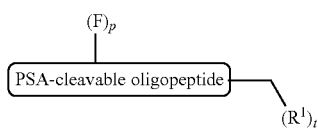

or a salt thereof, wherein:
p is 1, 2, 3, 4, or 5;
t is 1, 2, 3, or 4;
the PSA-cleavable oligopeptide is a mono- or multi-valent radical of an oligopeptide selected from the following:

```
                                                  (SEQ ID NO: 1)
Ac-Lys-Hyp-Ser-Ser-Chg-Gln-Ser-Ser-Lys-NH2, (SEQ ID NO: 2)
Gly-Hyp-Ala-Ser-Chg-Gln-Ser-Ser-Lys-NH2, (SEQ ID NO: 3)
Gly-Hyp-Ala-Ser-Chg-Gln-Ser-Ser-Lys, (SEQ ID NO: 4)
Hyp-Ser-Ser-Chg-Gln-Ser-Ser-Lys, (SEQ ID NO: 5)
Ac-Lys-Hyp-Ser-Ser-Chg-Gln-Ser-Ser-Lys, (SEQ ID NO: 6)
Ac-Lys-Hyp-Ala-Ser-Chg-Gln-Ser-Ser-Lys, (SEQ ID NO: 7)
Gly-Ser-Ser-Chg-Gln-Ser-Ser-Lys, (SEQ ID NO: 8)
Gly-Ser-Ser-Phe-Gln-Ser-Ser-Lys, (SEQ ID NO: 9)
Ac-Lys-Ala-Ser-Phe-Gln-Ser-Leu-Lys, (SEQ ID NO: 10)
Hyp-Ser-Chg-Gln-Ser-Lys, (SEQ ID NO: 11)
Ac-Lys-Hyp-Ser-Ser-Phe-Gln-Ser-Ser-Lys, (SEQ ID NO: 12)
Gly-Ala-Ser-Chg-Gln-Ser-Ser-Lys,
and
                                                  (SEQ ID NO: 13)
Gly-Hyp-Ser-Ser-Chg-Gln-Ser-Ser-Lys;
```

$R^1$ is hydrogen, —($C_{1-6}$ alkylene)-methoxypolyethylene glycol, or —($C_{1-6}$ alkylene)-N(R*)C(O)—($C_{1-6}$ alkylene)-N(—($C_{1-6}$ alkylene)-methoxypolyethylene glycol)C(O)—($C_{1-6}$ alkylene)-methoxypolyethylene glycol;
R* is hydrogen or unsubstituted $C_{1-6}$ alkyl;
F represents independently for each occurrence structural Formula IIIa or IIIb:

wherein:
$R^2$ represents independently for each occurrence hydrogen or unsubstituted $C_{1-6}$ alkyl, or two adjacent occurrences of $R^2$ are taken together with the atoms to which they are attached to form a 5- or 6-membered carbocyclic ring;
$R^3$ represents independently for each occurrence hydrogen or unsubstituted $C_{1-6}$ alkyl, or
$R_3$ and an adjacent occurrence of $R^2$ are taken together with the atoms to which they are attached to form a 5- or 6-membered carbocyclic ring;
$R^4$ is hydrogen or unsubstituted $C_{1-6}$ alkyl;
$R^5$ represents independently for each occurrence unsubstituted $C_{1-6}$ alkyl, unsubstituted $C_{1-6}$ alkyl-$SO_3^-M^+$, or unsubstituted $C_{1-6}$ alkyl-$SO_3H$;
$R^6$ and $R^7$ each represent independently for each occurrence occurrence hydrogen, —$SO_3H$, or —$SO_3^-M^+$;
M is a monovalent cation or absent;
n is 1, 2, or 3;
W represents a benzo-condensed, a naphtho-condensed, or a pyrido-condensed ring;
X represents independently for each occurrence C($CH_2Y_1$)($CH_2Y_2$), O, or S; and
$Y_1$ and $Y_2$ are independently hydrogen or unsubstituted $C_{1-6}$ alkyl; and Formula IIIb is represented by:

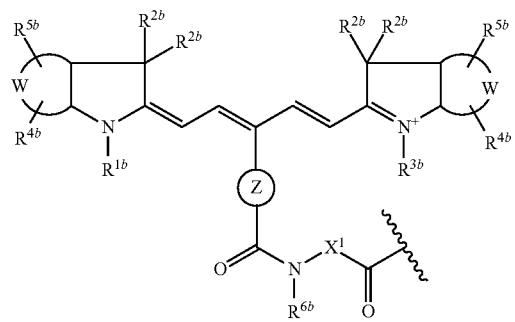

wherein:
$R^{1b}$ and $R^{3b}$ each represent independently unsubstituted $C_{1-6}$ alkyl, unsubstituted $C_{1-6}$ alkyl-$SO_3^-M^+$, or unsubstituted $C_{1-6}$ alkyl-$SO_3H$;
$R^{2b}$ each represents independently for each occurrence methyl, ethyl, or propyl;
$R^{4b}$ and $R^{5b}$ each represent independently for each occurrence hydrogen, —$SO_3H$, or —$SO_3^-M^+$;
$R^{6b}$ is hydrogen or $C_{1-6}$ unsubstituted alkyl;
M is a monovalent cation or absent;
W represents a benzo-condensed, a naphtho-condensed, or a pyrido-condensed ring;
Z is arylene; and
$X^1$ is unsubstituted $C_{1-8}$ alkylene.

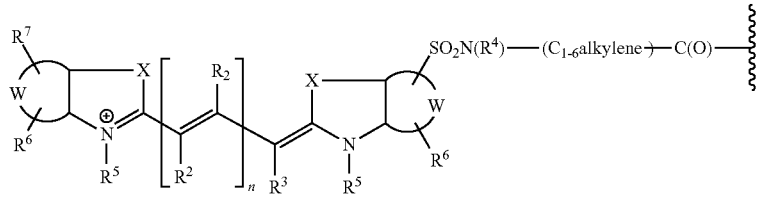

The description above for Formulae II and III describe multiple embodiments. All combinations of the embodiments are expressly contemplated. Further, because the definitions of the variables in Formulae II above encompass multiple chemical groups, the application contemplates embodiments where, for example, (i) the definition of a variable is a single chemical group selected from those chemical groups set forth above, (ii) the definition is a collection of two or more of the chemical groups selected from those set forth above, and (iii) the compound is defined by a combination of variables in which the variables are defined by (i) or (ii).

H. Exemplary Prostate Specific Antigen Activatable Agents

Useful prostate specific antigen activatable agents can be created using one or more of the prostate specific antigen targeting moieties, imaging reporters, biological modifiers, and linkers described hereinabove using standard chemistries known in the art. Depending upon the particular application, the prostate specific antigen activatable agents can be designed to be water soluble or water dispersible (i.e., sufficiently soluble or suspendable in aqueous or physiological media solutions). The prostate specific antigen activatable agents preferably do not have any undesired phototoxic properties and/or display low serum protein binding affinity. Exemplary specified prostate specific antigen activatable agents are listed in Table 4. In certain embodiments, the prostate specific antigen activatable agent is a prostate specific antigen activatable agent listed in Table 4 or a salt thereof.

TABLE 4*

| Compound No. | Chemical Structure |
| --- | --- |
| A1 | Ac-Lys(F2*)-Hyp-Ser-Ser-Chg-Gln-Ser-Ser-Lys(F2*)-NH$_2$ (SEQ ID NO: 36) |
| A2 | F4*-Gly-Hyp-Ala-Ser-Chg-Gln-Ser-Ser-Lys(F4*)-NH$_2$ (SEQ ID NO: 37) |
| A3 | F2*-Gly-Hyp-Ala-Ser-Chg-Gln-Ser-Ser-Lys(F2*)-NH-(mPEG 20,000) (SEQ ID NO: 38) |
| A4 | Ac-lys(F4*)-Hyp-Ser-Ser-Chg-Gln-Ser-Ser-Lys(F4*)-NH-(mPEG 20,000) (SEQ ID NO: 39) |
| A5 | F8*-Hyp-Ser-Ser-Chg-Gln-Ser-Ser-Lys(F8*)-NH-(mPEG 10,000) (SEQ ID NO: 40) |
| A6 | Ac-lys(F8*)-Hyp-Ala-Ser-Chg-Gln-Ser-Ser-Lys(F8*)-NH-(mPEG 10,000) (SEQ ID NO: 41) |
| A7 | Ac-lys(F4*)-Hyp-Ser-Ser-Phe-Gln-Ser-Ser-Lys(F4*)-NH-(mPEF 20,000) (SEQ ID NO: 42) |
| A8 | F2*-Hyp-Ala-Ser-Phe-Gln-Ser-Ser-Lys(F2*)-NH-(mPEG 20,000) (SEQ ID NO: 43) |
| A9 | 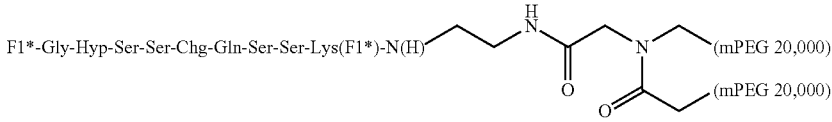 F1*-Gly-Hyp-Ser-Ser-Chg-Gln-Ser-Ser-Lys(F1*)-N(H)... (mPEG 20,000)/(mPEG 20,000) (SEQ ID NO: 44) |
| A10 | 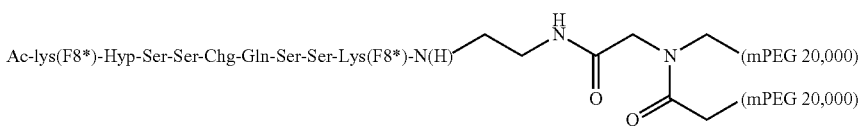 Ac-lys(F8*)-Hyp-Ser-Ser-Chg-Gln-Ser-Ser-Lys(F8*)-N(H)... (mPEG 20,000)/(mPEG 20,000) (SEQ ID NO: 45) |
| A11 | 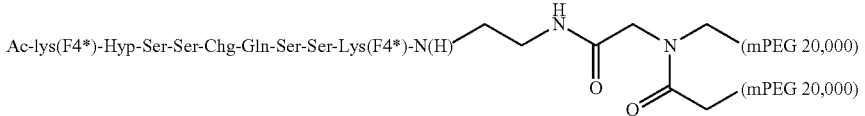 Ac-lys(F4*)-Hyp-Ser-Ser-Chg-Gln-Ser-Ser-Lys(F4*)-N(H)... (mPEG 20,000)/(mPEG 20,000) (SEQ ID NO: 46) |
| A12 | 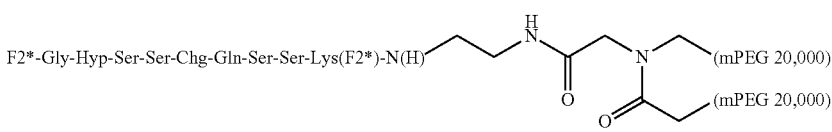 F2*-Gly-Hyp-Ser-Ser-Chg-Gln-Ser-Ser-Lys(F2*)-N(H)... (mPEG 20,000)/(mPEG 20,000) (SEQ ID NO: 47) |

*Structure of the F* portion of the chemical structure is provided below in Table 4A. The F* portion is covalently bound to the indicated amino acid residue to form an amide linkage.

TABLE 4A

| No. | Fluorophore Structure |
|---|---|
| F1* | |
| F2* | |
| F4* | |
| F8* | |

Exemplary prostate specific antigen activatable agents can include the following or a salt thereof:
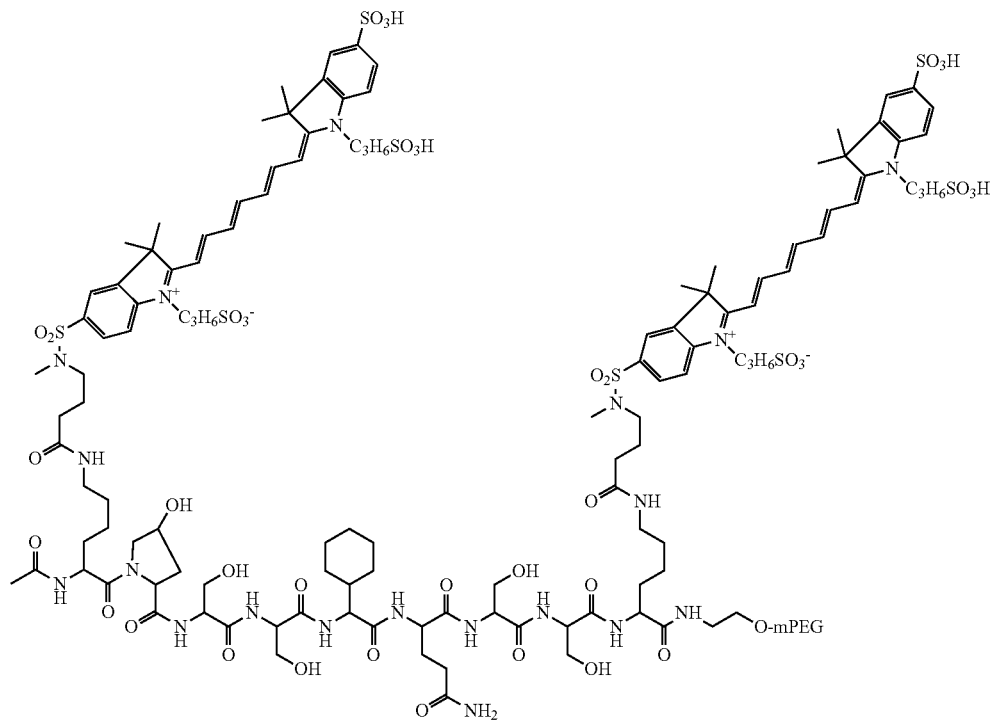
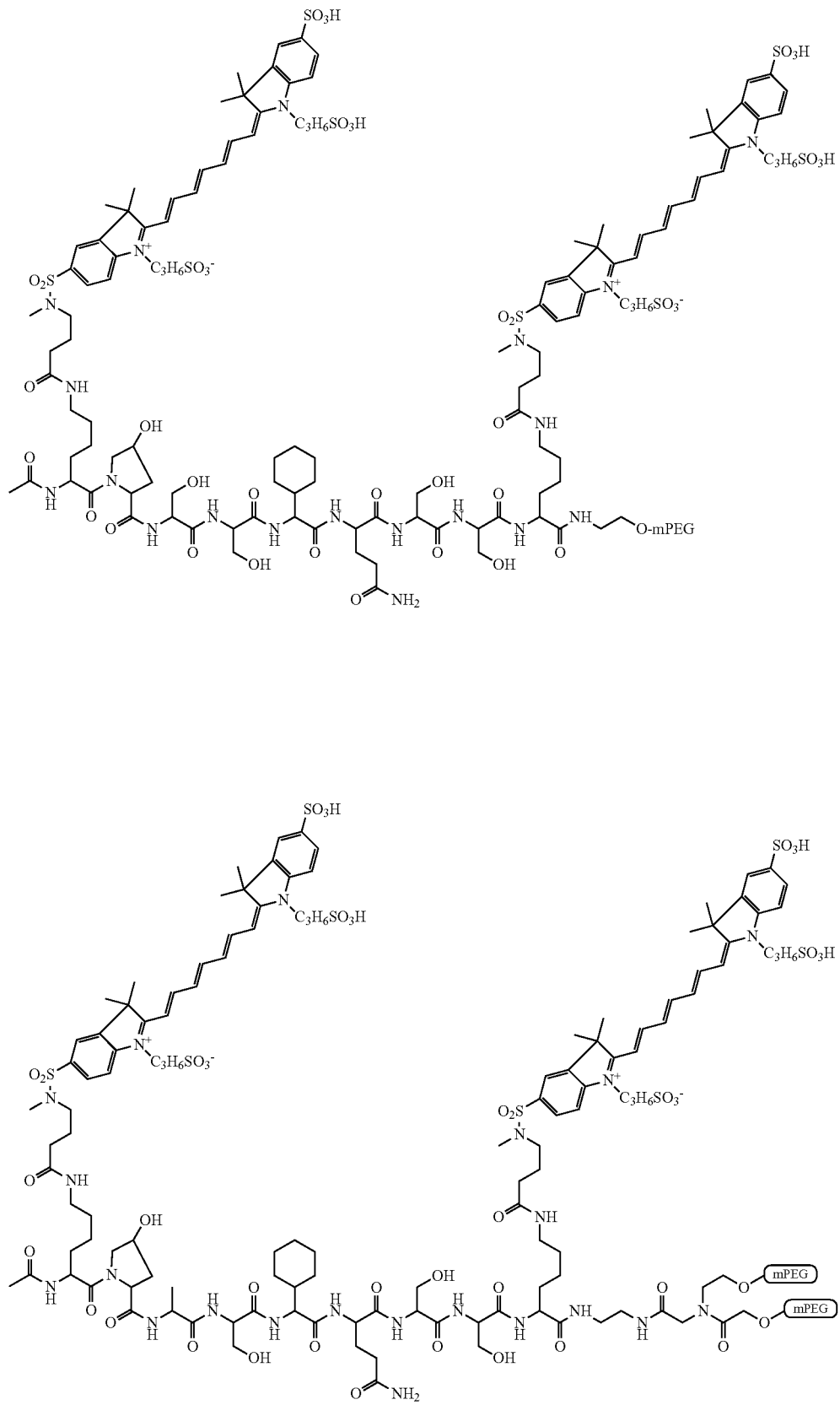

-continued

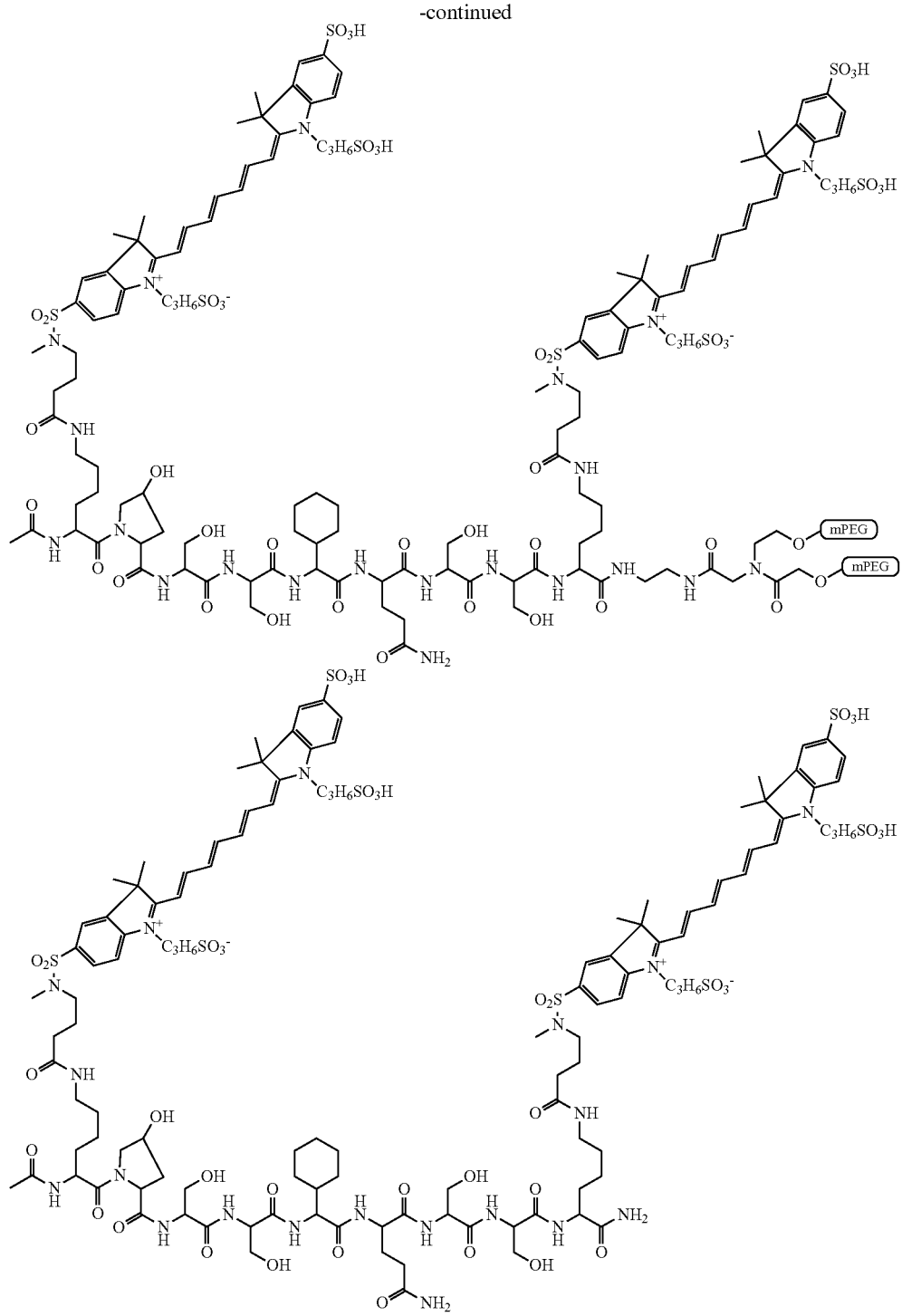

The imaging agents disclosed herein can be formulated into a pharmaceutical composition suitable for administration to a subject, for example, an animal and/or a human. The pharmaceutical composition can include one or more imaging agents and one or more excipients, for example, a stabilizer in a physiologically relevant carrier.

For in vivo use, the compositions of the present invention can be provided in a formulation suitable for administration to a subject, for example, an animal or a human. Accordingly, the formulations include the agents together with a physiologically relevant carrier suitable for the desired form and/or dose of administration. The term, "physiologically relevant carrier" is understood to mean a carrier in which the agents are dispersed, dissolved, suspended, admixed and physiologically tolerable, i.e., can be administered to, in, or on the subject's body without undue discomfort, or irritation, or toxicity. The preferred carrier is a fluid, preferably a liquid, more preferably an aqueous solution; however, carriers for solid formulations, topical formulations, inhaled formulations, ophthalmic formulations, and transdermal formulations are also contemplated as within the scope of the invention.

It is contemplated that the agents can be administered orally or parenterally. For parenteral administration, the agents can be administered intravenously, intramuscularly, cutaneously, percutaneously, subcutaneously, rectally, nasally, vaginally, and ocularly. Thus, the composition may be in the form of, e.g., solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The pharmaceutical compositions can be formulated according to conventional pharmaceutical practice (see, e.g., Remington: The Science and Practice of Pharmacy, 20th edition, 2000, ed. A. R. Germaro, Lippincott Williams & Wilkins, Philadelphia, and Encyclopedia of Pharmaceutical Technology, eds. J. Swarbrick and J. C. Boylan, 1988-1999, Marcel Dekker, New York).

It is understood that the formulation of the agents, the choice of mode of administration, the dosages of agents administered to the subject, and the timing between administration of the agents and imaging is within the level of skill in the art.

II. APPLICATIONS

It is understood that prostate specific antigen activatable agents can be used in a variety of imaging and therapeutic applications.

A. General Imaging Methods

The present invention provides methods for in vitro and in vivo imaging using the imaging agents disclosed herein. For a review of optical imaging techniques, see, e.g., Alfano et al., *Ann. NY Acad. Sci.* 820:248-270 (1997); Weissleder, *Nature Biotechnology* 19, 316-317 (2001); Ntziachristos et al., *Eur. Radiol.* 13:195-208 (2003); Graves et al., *Curr. Mol. Med.* 4:419-430 (2004); Citrin et al., *Expert Rev. Anticancer Ther.* 4:857-864 (2004); Ntziachristos, Ann. Rev. Biomed. Eng. 8:1-33 (2006); Koo et al., *Cell Oncol.* 28:127-139 (2006); and Rao et al., *Curr. Opin. Biotechnol.* 18:17-25 (2007).

Optical imaging includes all methods from direct visualization without use of any device and use of devices such as various scopes, catheters and optical imaging equipment, for example computer based hardware for tomographic presentations. The imaging agents are useful with optical imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

An imaging system useful in the practice of the invention typically includes three basic components: (1) an appropriate light source for inducing excitation of the imaging agent, (2) a system for separating or distinguishing emissions from light used for fluorophore excitation, and (3) a detection system. The detection system can be hand-held or incorporated into other useful imaging devices, such as intraoperative microscopes. Exemplary detection systems include an endoscope, catheter, tomographic system, hand-held imaging system, or an intraoperative microscope.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., *Proc. Natl. Acad. Sci. USA* 91:4887-4891, 1994; Ntziachristos et al., *Proc. Natl. Acad. Sci. USA* 97:2767-2772, 2000; and Alexander, *J. Clin. Laser Med. Surg.* 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light/signal detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al., *J. Photochem. Photobiol. B* 52:131-135, 1999), ovarian cancer (Major et al., *Gynecol. Oncol.* 66:122-132, 1997), colon and rectum (Mycek et al., *Gastrointest. Endosc.* 48:390-394, 1998; and Stepp et al., *Endoscopy* 30:379-386, 1998), bile ducts (Izuishi et al., *Hepatogastroenterology* 46:804-807, 1999), stomach (Abe et al., *Endoscopy* 32:281-286, 2000), bladder (Kriegmair et al., *Urol. Int.* 63:27-31, 1999; and Riedl et al., *J. Endourol.* 13:755-759, 1999), lung (Hirsch et al., *Clin Cancer Res* 7:5-220, 2001), brain (Ward, *J. Laser Appl.* 10:224-228, 1998), esophagus, and head and neck regions can be employed in the practice of the present invention.

Other types of light gathering components are catheter-based devices, including fiber optics devices. Such devices are particularly suitable for intravascular imaging. See, e.g., Tearney et al., *Science* 276:2037-2039, 1997; and Circulation 94:3013, 1996.

Still other imaging technologies, including phased array technology (Boas et al., Proc. Natl. Acad. Sci. USA 91:4887-4891, 1994; Chance, Ann. NY Acad. Sci. 838:29-45, 1998), optical tomography (Cheng et al., Optics Express 3:118-123, 1998; and Siegel et al., Optics Express 4:287-298, 1999), intravital microscopy (Dellian et al., Br. J. Cancer 82:1513-1518, 2000; Monsky et al., Cancer Res. 59:4129-4135, 1999; and Fukumura et al., Cell 94:715-725, 1998), confocal imaging (Korlach et al., Proc. Natl. Acad. Sci. USA 96:8461-8466, 1999; Rajadhyaksha et al., J. Invest. Dermatol. 104:946-952, 1995; and Gonzalez et al., J. Med. 30:337-356, 1999) and fluorescence molecular tomography (FMT) (Nziachristos et al., Nature Medicine 8:757-760, 2002; U.S. Pat. No. 6,615, 063, PCT WO 03/102558, and PCT WO 03/079015) can be used with the imaging agents of the invention. Similarly, the imaging agents can be used in a variety of imaging systems, for example, (1) the IVIS® Imaging Systems: 100 Series, 200 Series (Xenogen, Alameda, Calif.), (2) SPECTRUM and LUMINA (Xenogen, Alameda, Calif.), (3) the SoftScan® or the eXplore Optix™ (GE Healthcare, United Kingdom), (4) Maestro™ and Nuance™-2 Systems (CRi, Woburn, Mass.), (5) Image Station In-Vivo FX from Carestream Molecular Imaging, Rochester, N.Y. (formerly Kodak Molecular Imaging Systems), (6) OV100, IV 100 (Olympus Corporation, Japan), (7) Cellvizio Mauna Kea Technologies, France), (8)] NanoSPECT/CT or HiSPECT (Bioscan, Washington, D.C.), (9) CTLM® or LILA™ (Imaging Diagnostic Systems, Plantation, Fla.), (10) DYNOT™ (NIRx Medical Technologies, Glen Head, N.Y.), and (11) NightOWL Imaging Systems by Berthold Technologies, Germany.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

For agents that have magnetic properties, MRI imaging well known in the art can also be applied in the practice of the invention. For a review of MRI techniques see Westbrook, Handbook of MRI Technique, $2^{nd}$ Edition, 1999, Blackwell Science. It is possible that images obtained, for example, by optical imaging and by magnetic resonance imaging can be co-registered or fused with one another to provide additional information about the item being imaged. Furthermore, multi-modality imaging systems (i.e., combined optical and MR imaging systems) can be used to create combined optical MR images.

In addition, the compositions and methods of the present invention can be used for other imaging compositions and methods.

In addition, the compositions and methods of the present invention can be used in combination with other imaging compositions and methods. For example, the agents of the present invention can be imaged by optical imaging protocols either alone or in combination with other traditional imaging modalities, such as, X-ray, computed tomography (CT), MR imaging, ultrasound, positron emission tomography (PET), and single photon computerized tomography (SPECT). For instance, the compositions and methods of the present invention can be used in combination with CT or MRI to obtain both anatomical and molecular information simultaneously, for example, by co-registration of with an image generated by another imaging modality. The compositions and methods of the present invention can also be used in combination with X-ray, CT, PET, ultrasound, SPECT and other optical and MR contrast agents or alternatively, the agents of the present invention may also include imaging agents, such as iodine, gadolinium atoms and radioactive isotopes, which can be detected using CT, PET, SPECT, and MR imaging modalities in combination with optical imaging. The imaging agents can be linked to or incorporated in the agents.

(i) In Vivo Imaging Methods

With respect to optical in vivo imaging, such a method comprises (a) administering to a subject one or more of the prostate specific antigen activatable agents described herein, (b) allowing sufficient time to permit the agent to distribute with the subject, and (c) detecting a signal emitted by the prostate specific antigen activatable agent. The signal emitted by the agent can be used to construct an image, for example, a tomographic image. The foregoing steps can be repeated at predetermined time intervals thereby to permit evaluation of the emitted signals of the prostate specific antigen activatable agents in the subject over time.

In another in vivo imaging method, the method comprises (a) administering to a subject one or more of the prostate specific antigen activatable agents described herein that contains a fluorochrome; (b) allowing sufficient time to permit the prostate specific antigen activatable agent to distribute within the subject; (c) exposing the subject to light of a wavelength absorbable by the fluorochrome, and (d) detecting a signal emitted by the prostate specific antigen activatable agent. The foregoing steps can be repeated at predetermined time intervals thereby to permit evaluation of the emitted signals of the prostate specific antigen activatable agents in the subject over time. The illuminating and/or detecting steps (steps (c) and (d), respectively) can be performed using an endoscope, catheter, tomographic system, planar system, hand-held imaging system, goggles, or an intraoperative microscope.

Before or during these steps, a detection system can be positioned around or in the vicinity of a subject (for example, an animal or a human) to detect signals emitted from the subject. The emitted signals can be processed to construct an image, for example, a tomographic image. In addition, the processed signals can be displayed as images either alone or as fused (combined) images.

In addition, it is possible to practice an in vivo imaging method that selectively detects and images one, two or more molecular imaging probes, including the prostate specific antigen activatable agents simultaneously. In such an approach, for example, in step (a) noted above, two or more imaging probes whose signal properties are distinguishable from one another are administered to the subject, either at the same time or sequentially, wherein at least one of the molecular imaging probes is a prostate specific antigen activatable agent. The use of multiple probes permits the recording of multiple biological processes, functions or targets.

The subject may be a vertebrate, for example, a mammal, for example, a human. The subject may also be a non-vertebrate (for example, *C. elegans, Drosophila*, or another model research organism, etc.) used in laboratory research.

Information provided by such in vivo imaging approaches, for example, the presence, absence, or level of emitted signal can be used to detect and/or monitor a disease in the subject. Exemplary diseases include, without limitation cancer. In addition, in vivo imaging can be used to assess the effect of a compound or therapy by using the imaging agents, wherein the subject is imaged prior to and after treatment with the compound or therapy, and the corresponding signal/images are compared.

The prostate specific antigen activatable agents also can be used in in vivo imaging method where cells labeled with the prostate specific antigen activatable agent are administered to the recipient. The cells can be labeled with the prostate specific antigen activatable agents either in vivo or ex vivo. In the ex vivo approach, cells can be derived directly from a subject or from another source (e.g., from another subject, cell culture, etc.). The prostate specific antigen activatable agents can be mixed with the cells to effectively label the cells and the resulting labeled cells administered to the subject into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

It is understood that the formulation of the prostate specific antigen activatable agents, the choice of mode of administration, the dosages of prostate specific antigen activatable agents administered to the subject, and the timing between administration of the prostate specific antigen activatable agents and imaging is within the level of skill in the art.

The foregoing methods can be used to determine a number of indicia, including tracking the localization of the prostate specific antigen activatable agent in the subject over time or assessing changes or alterations in the metabolism and/or excretion of the prostate specific antigen activatable agent in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions of the invention can be used to help a physician or surgeon to identify and characterize areas of disease, such as dysplasia and cancer, to distinguish diseased from normal tissues, such as detecting specific regions of prostate cancer within an organ or other tissues that are difficult to detect using ordinary imaging techniques, and to further assess said tissues as candidates for particular treatment regimens, or gauge the prognosis such as likelihood of sepsis.

The methods and compositions of the invention can also be used in the detection, characterization and/or determination of the localization of a disease, including early disease, the severity of a disease or a disease-associated condition, the staging of a disease, and/or monitoring a disease. The presence, absence, or level of an emitted signal can be indicative of a disease state.

The methods and compositions of the invention can also be used to monitor and/or guide various therapeutic interventions, such as surgical procedures, and monitoring drug therapy, including cell based therapies. The methods described herein can also be used to assess therapeutic efficacy of various treatment regimens, including but not limited to those designed to reduce tumor acidosis and metastasis or various radiotherapeutics. The methods of the invention can also be used in prognosis of a disease or disease condition.

The methods and compositions described herein can, therefore, be used, for example, to detect and/or quantify the presence and/or localization of elevated prostate specific antigen in a subject, including humans, for instance in cancerous cells or tissues, and to detect and/or quantify the presence and/or localization of prostate specific antigen, including the presence of dysplastic areas within an organ. The methods and compositions described herein can also be used to detect and/or quantify prostate specific antigen associated with diseases, disorders and conditions, including but not limited to preneoplastic/neoplastic disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of neoplasia, dysplasia, and cancer, such as prostate cancer. The methods and compositions can also be used for drug delivery and to monitor drug delivery, especially when drugs or drug-like molecules are chemically attached to the fluorescent probes. Exemplary drug molecules include chemotherapeutic and cytostatic agents and photodynamic agents including but not limited to Photofrin, Lutrin, Antrin, aminolevulinic acid, hypericin, benzoporphyrin derivative, and porphyrins.

In addition, the methods and compositions described herein can be used to image the enzymatically active prostate specific antigen levels in a subject. The method comprises administering to a subject (for example, a human or animal) an amount of one or more of the prostate specific antigen activatable agents described herein sufficient to facilitate prostate specific antigen imaging. After sufficient time to permit the agent to distribute within the animal or distribute within the area to be imaged, the presence and/or amount of the agent is determined. The presence and/or amount of the agent can then be used to create an image, for example, a tomographic image, representative of elevated positively charged cell surfaces within the tissues of the subject.

(ii) In Vitro Imaging Methods

With respect to in vitro imaging, the imaging agents can be used in a variety of in vitro assays. For example, an exemplary in vitro imaging method comprises: (a) contacting a sample, for example, a biological sample, with one or more of the prostate specific antigen activatable agents described herein; (b) allowing the agent(s) to interact with a biological target in the sample; (c) optionally, removing unbound agent; and (d) detecting a signal emitted from the agent thereby to determine whether the agent has been activated by or bound to the biological target. When the prostate specific antigen activatable agent comprises a fluorochrome, step (d) further comprises illuminating the sample with light of a wavelength absorbable by the fluorochrome to produce the emitted signal.

After an agent has been designed, synthesized, and optionally formulated, it can be tested in vitro by one skilled in the art to assess its biological and performance characteristics. For instance, different types of cells grown in culture can be used to assess the biological and performance characteristics of the agent. Cellular uptake, binding or cellular localization of the agent can be assessed using techniques known in the art, including, for example, fluorescent microscopy, FACS analysis, immunohistochemistry, immunoprecipitation, in situ hybridization and Forster resonance energy transfer (FRET) or fluorescence resonance energy transfer. By way of example, the agents can be contacted with a sample for a period of time and then washed to remove any free agents. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the agents. Other detection methods including, but not limited to flow cytometry, immunoassays, hybridization assays, and microarray analysis can also be used.

B. Exemplary Imaging Methods

One aspect of the invention provides a method of in vivo imaging, the method comprising: (a) administering to a subject a prostate specific antigen imaging agent; (b) allowing the agent to distribute within the subject; and (c) detecting a signal emitted by the prostate specific antigen imaging agent.

Another aspect of the invention provides a method of in vivo optical imaging, the method comprising: (a) administering to a subject a prostate specific antigen imaging agent, wherein the agent comprises a fluorochrome; (b) allowing the agent to distribute within the subject; (c) exposing the subject to light of a wavelength absorbable by the fluorochrome; and (d) detecting a signal emitted by the agent.

Another aspect of the invention provides a method of in vivo imaging, wherein the signal emitted by the agent is used to construct an image. In other embodiments, the image is a tomographic image. In certain embodiments, the invention is a method of in vivo optical imaging, wherein steps (a)-(c) are repeated at predetermined time intervals thereby to permit evaluation of the emitted signals of the prostate specific antigen activatable agent in the subject over time. In certain embodiments, the invention is a method of in vivo optical imaging, wherein steps (a)-(d) are repeated at predetermined time intervals thereby to permit evaluation of the emitted signals of the prostate specific antigen activatable agents in the subject over time. In certain embodiments, the invention is a method of in vivo imaging, wherein the subject is an animal or a human. In certain embodiments, the invention is a method of in vivo imaging, wherein in step (a) two or more imaging probes whose signal properties are distinguishable from one another are administered to a subject, wherein at least one of the imaging probes is a prostate specific antigen activatable agent. In certain embodiments, the invention is a method of in vivo optical imaging, wherein the illuminating and detecting steps are performed using an endoscope, catheter, tomographic system, hand-held optical imaging system, or an intraoperative microscope.

Another aspect of the invention provides a method of in vivo imaging, wherein the presence, absence, or level of emitted signal is indicative of a disease state. In certain embodiments, the invention is a method of in vivo imaging, wherein the method is used to detect and/or monitor a disease. In certain embodiments, the disease is selected from the group consisting of dysplasia, neoplasia, prostate cancer and cancer. The agents described here are used for imaging sites of active PSA as a means for detecting prostate cancer.

Another aspect of the invention provides a method of in vivo imaging, wherein, in step (a), cells labeled with the prostate specific antigen activatable agent are administered to the subject. In other embodiments, the signal emitted by the prostate specific antigen activatable agent is used to monitor trafficking and localization of the cells.

Another aspect of the invention provides a method of imaging enzymatically active prostate specific antigen levels in a subject, the method comprising the steps of: (a) administering an agent to a subject; and (b) detecting the presence of the agent thereby to produce an image representative of ezymatically active prostate specific antigen concentration. In certain embodiments, the invention is a method of treating a disease in a subject comprising administering to a subject, either systemically or locally, an agent, wherein the agent comprises a radiolabel that localizes in the disease area and delivers an effective dose of radiation.

Another aspect of the invention provides an in vitro imaging method, the method comprising: (a) contacting a sample with an agent; (b) allowing the agent to bind to a biological target; (c) optionally removing unbound agent; and (d) detecting signal emitted from the agent thereby to determine whether the agent has been activated by or bound to the biological target. In other embodiments, the sample is a biological sample.

In certain embodiments, the chemical modifying groups comprise a biologically active molecule, such as a drug or a radiotherapeutic moiety. In certain embodiments the biologically active molecule is linked to the agent through a linker that is cleavable through a biological or physical mechanism including but not limited to enzymatic, thermal, acid catalyzed or photochemical cleavage.

In certain preferred embodiments, Q can be selected from a group consisting of (i) a substituted or unsubstituted aryl, (ii) a functionalized, substituted or unsubstituted heteroaryl, (iii) a functionalized, substituted or unsubstituted $C_1$-$C_{18}$ alkyl, alkenyl, alkynyl, alkoxy, or thioalkyl group. In other embodiments, Q is absent.

In certain embodiments, the chemical modifying moiety, M enhances the binding selectivity of the prostate specific antigen activatable agent for enzymatically active prostate specific antigen over other proteins.

In certain embodiments, the chemical modifying moiety, M reduces the nonspecific enzymatic cleavage of the prostate specific antigen activatable agent. Furthermore, in other embodiments, the chemical modifying moiety, M reduces the nonspecific tissue accumulation of the prostate specific antigen activatable agent when administered to a live animal.

In one aspect of the invention, prostate specific antigen activatable agents are fluorescent in the far-red or near-infrared spectral range upon activation.

In certain embodiments, the prostate specific antigen activatable agent further comprises one or more chemical modifiers, independently, chemically linked to the prostate specific antigen targeting moiety, L, and/or F or any combination thereof.

C. Therapeutic Applications

Certain of the prostate specific antigen activatable agents described herein, for example, agents containing a radiolabel and drug molecule, can be used to ameliorate a symptom of, or treat, a particular disease or disorder. The method comprises (a) administering an amount of one or more the agents described herein sufficient to impart a therapeutic effect in the subject; and (b) permitting sufficient time for the agent to distribute within the subject or otherwise localize in a region of the subject to be treated and then, (c) depending on the therapeutic agent, optionally activating the agent to impart a therapeutic effect. For example, when the therapeutic agent is a radiolabel, no subsequent activation is required. However, when the therapeutic agent is a photoreactive agent, for example, a dye used in photodynamic therapy, the agent may be activated by exposing the agent to light having a wavelength that activates the agent. As a result, the agents can be used to treat a condition of interest, for example, a cancer, immune disorder, inflammatory disorder, vascular disorder and the like. Furthermore the agents can be used to inhibit dysplasia in an organ, or other region of interest in the subject, or reduce cancerous cell proliferation within a subject.

The invention will now be illustrated by means of the following examples, which are given for the purpose of illustration only and without any intention to limit the scope of the present invention.

III. PHARMACEUTICAL COMPOSITIONS

Agents described herein may be formulated with one or more pharmaceutically acceptable carriers (additives) and/or diluents to provide a pharmaceutical composition. Exemplary pharmaceutical compositions comprise one or more agents and one or more pharmaceutically acceptable carriers. As described in detail below, the pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically-acceptable carriers include a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical compositions of this invention suitable for parenteral administration comprise one or more agents of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In certain embodiments, the invention provides a pharmaceutically acceptable composition suitable for administration to a subject comprising a prostate specific antigen imaging agent and a pharmaceutically acceptable excipient.

IV. DEFINITIONS

To facilitate an understanding of the present invention, a number of terms and phrases are defined below.

The terms "a," "an" and "the" as used herein mean "one or more" and include the plural unless the context is inappropriate.

As used herein, the term "effective amount" refers to the amount of a compound sufficient to effect beneficial or desired results. Unless stated otherwise, an effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "patient" and "subject" refer to organisms to be treated by the methods of the present invention. Such organisms preferably include, but are not limited to, mammals (e.g., murines, simians, equines, bovines, porcines, canines, felines, and the like), and most preferably includes humans.

Certain compounds described herein may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The term "affinity" as used herein, refers to the ability of the prostate specific antigen activatable agent to bind to and/or be retained by a prostate specific antigen.

As used herein, the term "functionality" is understood to mean a reactive functional group that can be further modified or derivatized with another molecule. In one aspect, the reactive functional group is an amine, carboxylic acid, carboxylic ester, halogen, hydrazine, hydroxylamine, nitrile, isonitrile, isocyanate, isothiocyanate, thiol, maleimide, azide, alkyne, tetrazolyl, phosphonate, alkene, nitro, and nitroso.

The term "alkyl" is art-recognized, and includes saturated aliphatic groups, including straight-chain alkyl groups, and branched-chain alkyl groups. Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. In certain embodiments, the alkyl is unsubstituted.

The term "alkylene" refers to a diradical of an alkyl group. Exemplary alkylene groups include —$CH_2$— and —$CH_2CH_2$—.

The term "heteroalkyl" is art-recognized and refers to saturated aliphatic groups, including straight-chain alkyl groups, and branched-chain alkyl groups where one of the backbone carbon atoms has been replaced with a heteroatom, such as O, S, or N. Exemplary heteroalkyl groups include —$CH_2$—O—$CH_3$ and —$CH_2CH_2$—O—$CH_3$.

The term "heteroalkylene" refers to a diradical of an heteroalkyl group. Exemplary heteroalkylene groups include —$CH_2$—O—$CH_2$— and —$CH_2CH_2$—O—$CH_2$—.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "arylene" as used herein refers to a divalent radical of an aromatic group. Arylene may be optionally substituted as described for aryl, or as otherwise indicated. An exemplary arylene group is

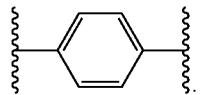

As used herein, the terms "heterocyclic" and "heterocyclyl" refer to an aromatic or nonaromatic ring containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic (or heterocyclyl) ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, aryl or heteroaryl moieties, —CF$_3$, —CN, or the like.

The terms "amine" and "amino" are art-recognized and refer to both unsubstituted and substituted amines, e.g., a moiety that may be represented by the general formulas:

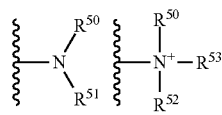

wherein $R^{50}$, $R^{51}$, $R^{52}$ and $R^{53}$ each independently represent a hydrogen, an alkyl, an alkenyl, —(CH$_2$)$_m$—R$^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—R$^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R$^{61}$, where m and $R^{61}$ are described above.

The term "substituted" refers to a group in which one or more hydrogen atoms are independently replaced with the same or different substituent(s). Exemplary substituents include, but are not limited to, halogen, alkyl, haloalkyl, oxo, alkoxyl, thiol, thioether, cyano, ester, ketone, amide, sulfonamide, carboxylate, carboxylic acid, aryl, aralkyl, alkenyl, alkynyl, alkylene-amide, etc.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula NW$_4^+$, wherein W is C$_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

V. EXAMPLES

The invention now being generally described, will be more readily understood by reference to the following examples, which are included merely for purposes of illustration of certain aspects and embodiments of the present invention, and are not intended to limit the invention.

Example 1

Exemplary Syntheses of PSA Activatable Agents

The compounds of the present invention can be synthesized from readily available starting materials following standard methods and procedures. The following non-limiting examples demonstrate the synthesis of exemplary fluorescent prostate specific antigen activatable agents. Representative materials and methods that may be used in preparing the materials of the invention are described further below. Unless otherwise stated, all chemicals and solvents (reagent grade) are used as commercially obtained without further purification. Synthesized compounds are characterized and purified by HPLC or ion-exchange column chromatography.

The N-hydroxysuccinimide ester (ie., NHS ester) of a fluorophore from Table 3 refers to the compound in which the carboxylic acid group of the fluorophore has been replaced with a N-hydroxysuccinimide ester. For example, the N-hydroxysuccinimide ester of fluorophore F2 has the following chemical structure:

The abbreviation "EDC" refers to 1-ethyl-3-(3-dimethylaminopropyl)carbodiimide. The abbreviation "HOBt" refers to hydroxybenzotriazole. The abbreviation Y-mPEG amine refers to the following compound:

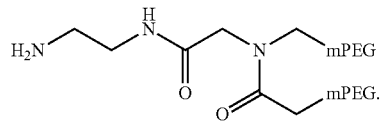

Part I: General Procedures:
General Method A for Peptide Conjugation.

A solution of fluorophore-NHS ester (~3 μmol) in dimethylformaide (DMF) was added to a solution of oligopeptide (1 μmol) in DMF (1 mL). After the reaction was complete, as judged by HPLC, the solution was diluted with aqueous sodium bicarbonate to hydrolyze excess fluorophore-NHS ester. The desired product was then isolated by preparatory HPLC.

General Method B for mPEG Amine Coupling.

To a solution of fluorophore-labeled peptide and mPEG amine (1.5 equiv) in DMF was added HOBt (1 equiv), N-methylmorpholine (2 equiv), and EDC (1.5 equiv). After the reaction was complete, the reaction mixture was diluted with water and the desired product isolated by ion-exchange column chromatography.

Part II: Synthesis of PSA Activatable Agent A1

Oligopeptide, SEQ ID NO:1 from Table 1 above, was conjugated with the N-hydroxysuccinimide ester of fluorophore F2 using general method A. The resulting crude product was purified by preparatory HPLC.

Part III: Synthesis of PSA Activatable Agent A3

Oligopeptide, SEQ ID NO:3 from Table 1 above, was conjugated with the NHS ester of F2 using general method A. After purification by preparatory HPLC, the conjugate was coupled with mPEG amine, ~20 kDa, using general method B. The resulting product was purified through ion-exchange column chromatography.

Example 2

Synthesis of PSA Activatable Agent A5

Oligopeptide, SEQ ID NO:4 from Table 1 above, was conjugated with the NHS ester of F8 using general method A from Example 1. After purification by preparatory HPLC, the conjugate was coupled with mPEG amine, ~10 kDa, using

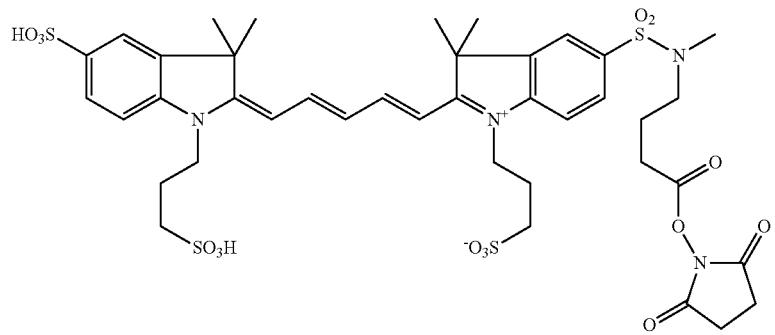

general method B from Example 1. The resulting product was purified through ion-exchange column chromatography.

Example 3

Synthesis of PSA Activatable Agent A10

Oligopeptide, SEQ ID NO:5 from Table 1 above, was conjugated with the NHS ester of F8 using general method A from Example 1. After purification by preparatory HPLC, the conjugate was coupled with Y-mPEG amine, ~40 kDa, using general method B from Example 1. The resulting product was purified through ion-exchange column chromatography.

Example 4

Synthesis of PSA Activatable Agent A12

Oligopeptide, SEQ ID NO:13 from Table 1 above, was conjugated with the NHS ester of F2 using general method A from Example 1. After purification by preparatory HPLC, the conjugate was coupled with Y-mPEG amine, ~40 kDa, using general method B from Example 1. The resulting product was purified through ion-exchange column chromatography.

Example 5

Prostate Specific Antigen Activatable Agents are Cleaved by Enzymatically Active PSA In Vitro This example demonstrates that the prostate specific antigen activatable agents described herein are cleaved by enzymatically active prostate specific antigen in vitro. Test agent (compound A10-0.5 µM final concentration of agent) was activated in the presence of active PSA (0.1 µM final concentration of activated enzyme) but not complexed PSA, in the optimized buffer (TCNB or 50 nM Tris, 10 mM $CaCl_2$, 150 mM NaCl, 0.05% Brij-35, pH 7.5) for each enzyme. Kinetic fluorescence readings were performed in a Gemini fluorescence plate reader at different times after adding the enzyme.

In this experiment, fluorescence is only associated with the test agents (compound A10) in the presence of active PSA described herein. The results, shown in FIG. 1, demonstrate in vitro activation of the prostate specific antigen activatable agents, such as compound A10 in the presence of active PSA.

Example 6

Figure 2A:
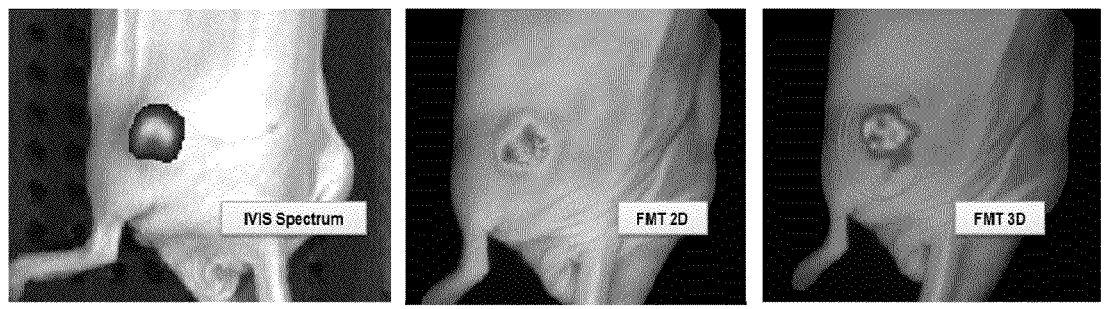
FIG. 2A depicts epi-fluorescent reflectance and tomographic images for sites of active PSA detected in prostate cancer expressing mice six hours post-injection using a prostate specific antigen activatable agent (compound A10).

In Vivo Imaging of Prostate Cancer Using Prostate Specific Antigen Activatable Agents As depicted in FIG. 2A, imaging studies were performed in human prostate $PSA^+$ LNCaP tumor-bearing male Nu/Nu mice. The mice were injected intravenously with 2 nmoles of test agent (compound A10) and were imaged 6 hours later on the FMT2500 (PerkinElmer Inc., Waltham, Mass.) (FMT 2D for epifluorescence, FMT 3D for tomography) in reflectance and tomographic modes, and on the IVIS Spectrum (PerkinElmer Inc., Waltham, Mass.). Sites of active PSA are detected in the same locations for both reflectance and tomographic imaging, thereby demonstrating the ability of the agent to detect enzymatically active PSA in vivo.

Example 7

Specificity of Prostate Specific Antigen Activatable Agents In Vivo

Figure 2B:
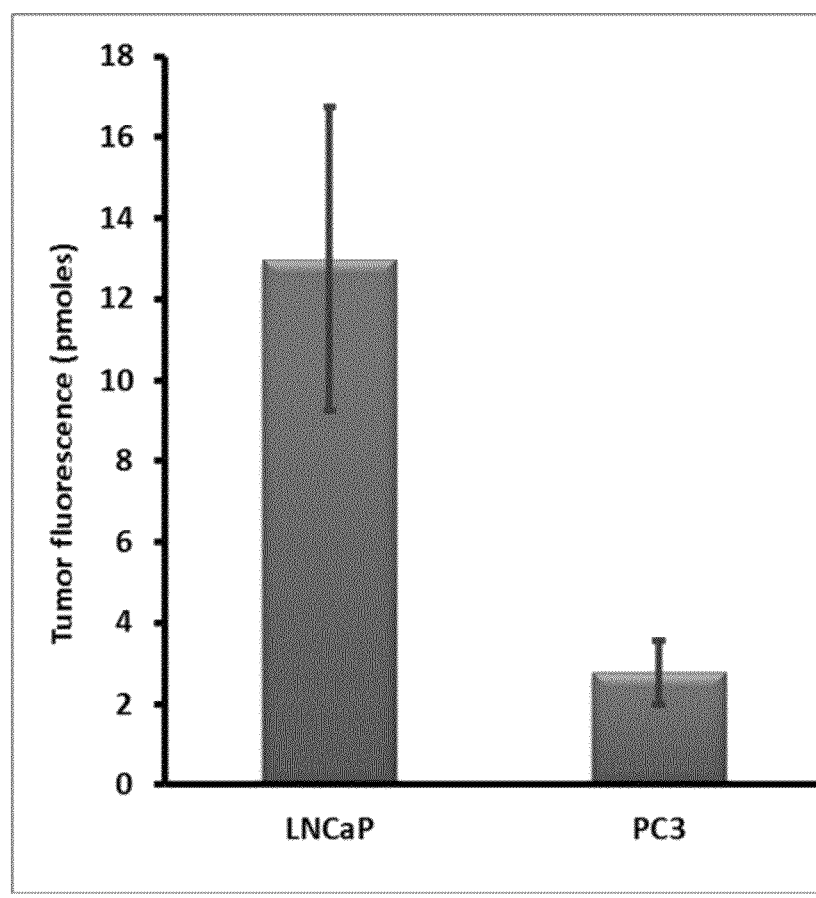
FIG. 2B is a histogram comparing fluorescence between prostate cancer expressing (PSA positive) and control (PSA negative) mice injected with the prostate specific antigen activatable agent (compound A10) and imaged tomographically.

Imaging studies were performed in LNCaP tumors (PSA+) and PC3 (PSA−) tumors tumor-bearing male Nu/Nu mice. The mice were injected intravenously with 2 nmoles of compound A10 and imaged 24 hours later on the FMT2500 (PerkinElmer Inc., Waltham, Mass.). Tumor fluorescence from positive and control mice was quantified and plotted. FIG. 2B demonstrates the specificity the prostate specific antigen activatable agents have for tumors containing enzymatically active PSA over PSA negative tumors in vivo.

INCORPORATION BY REFERENCE

All publications, patents, and patent applications cited herein are hereby expressly incorporated by reference in their entirety and for all purposes to the same extent as if each was so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

---

What is claimed is:

1. A prostate specific antigen (PSA) activatable agent represented by Formula II:

(II)

or a salt thereof, wherein:

$R^1$ is —($C_{1-6}$ alkylene)-methoxypolyethylene glycol, or —($C_{1-6}$ alkylene)-N($R^*$)C(O)—($C_{1-6}$ alkylene)-N(—($C_{1-6}$ alkylene)-methoxypolyethylene glycol)C(O)—($C_{1-6}$ alkylene)-methoxypolyethylene glycol;

$R^*$ is hydrogen or unsubstituted $C_{1-6}$ alkyl;

F represents independently for each occurrence the following structural formula:

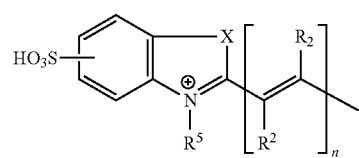

-continued

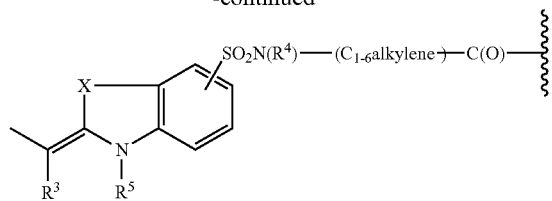

wherein:
$R^2$ represents independently for each occurrence hydrogen or unsubstituted $C_{1-6}$ alkyl, or two adjacent occurrences of $R^2$ are taken together with the atoms to which they are attached to form a 5- or 6-membered carbocylic ring;
$R^3$ is hydrogen or unsubstituted $C_{1-6}$ alkyl, or $R_3$ and an adjacent occurrence of $R^2$ are taken together with the atoms to which they are attached to form a 5- or 6-membered carbocylic ring;
$R^4$ is hydrogen or unsubstituted $C_{1-6}$ alkyl;
$R^5$ represents independently for each occurrence unsubstituted $C_{1-6}$ alkyl-$SO_3^-M^+$ or unsubstituted $C_{1-6}$ alkyl-$SO_3H$;
M is a monovalent cation or absent
n is 1, 2, or 3; and
X is $C(CH_3)_2$ or $C(CH_2CH_2$
the PSA-cleavable oligopeptide is one of the following:

(SEQ ID NO: 14)

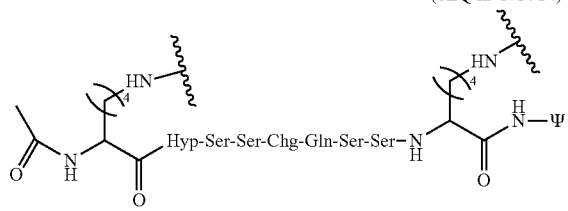

(SEQ ID NO: 19)

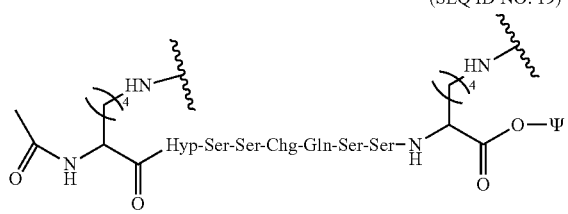

(SEQ ID NO: 32)

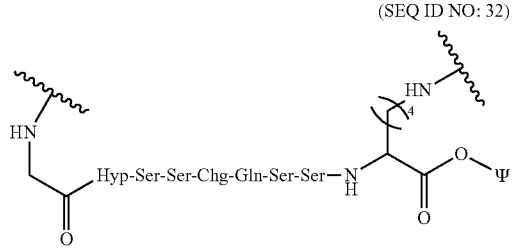

(SEQ ID NO: 33)

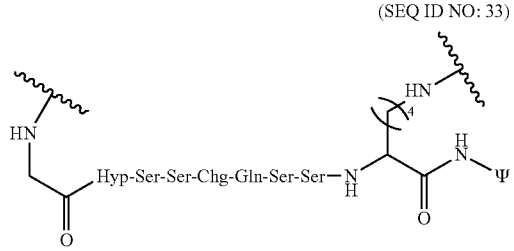

wherein ψ is a covalent bond to $R^1$.

2. An agent selected from the group consisting of A10 and A12 in Table 4 or a salt thereof.

3. The agent of claim 1, wherein the agent is one of the following or a salt thereof:

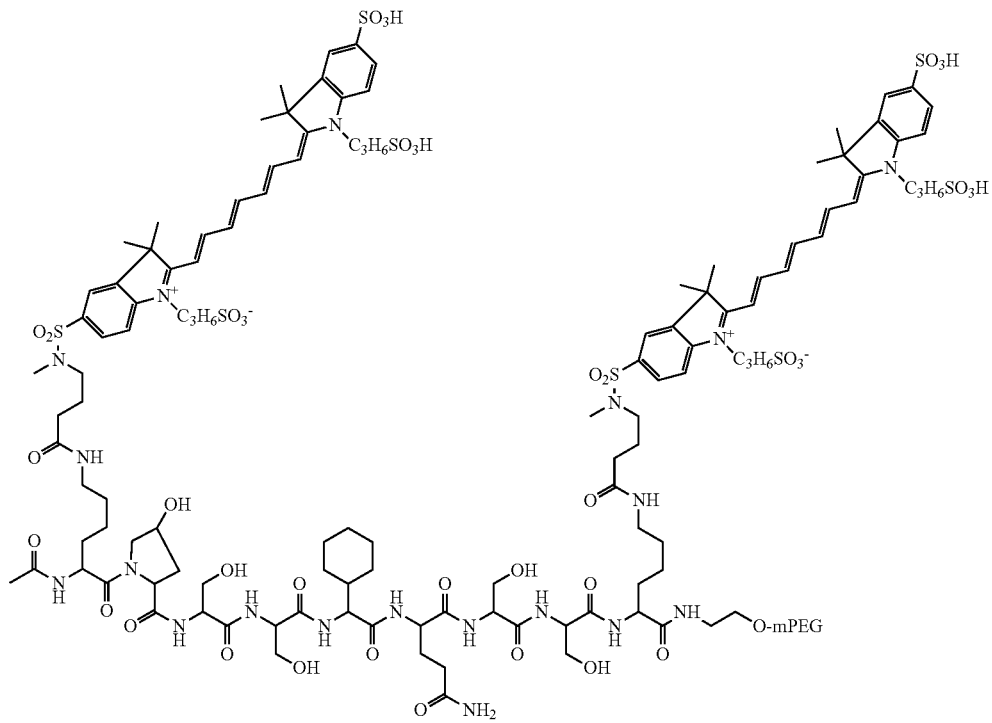

93 94
-continued
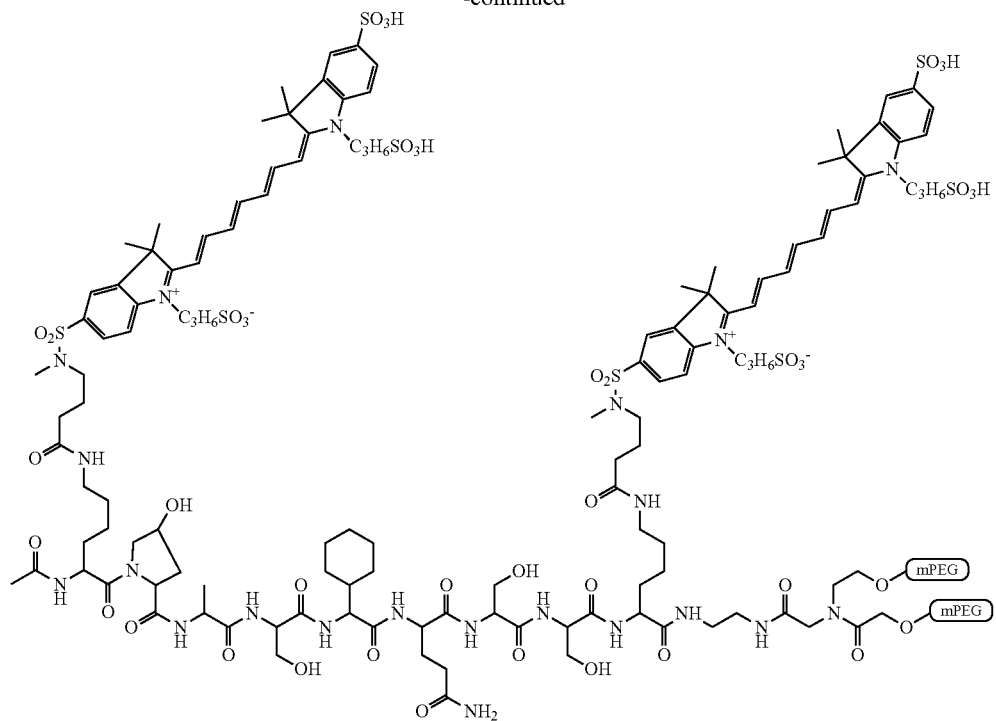
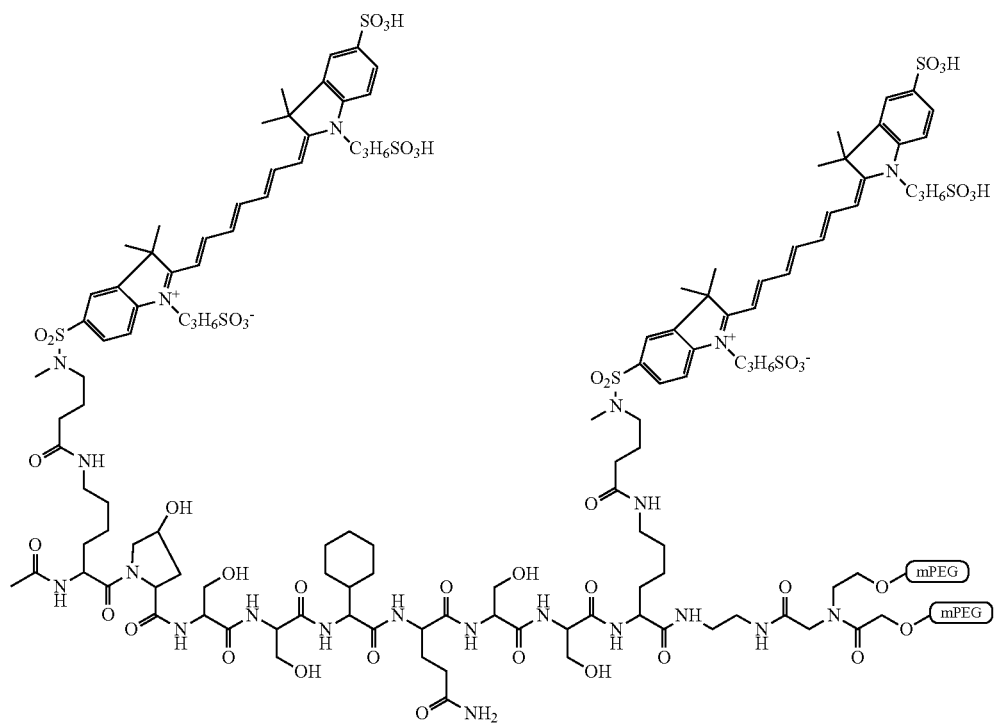

-continued

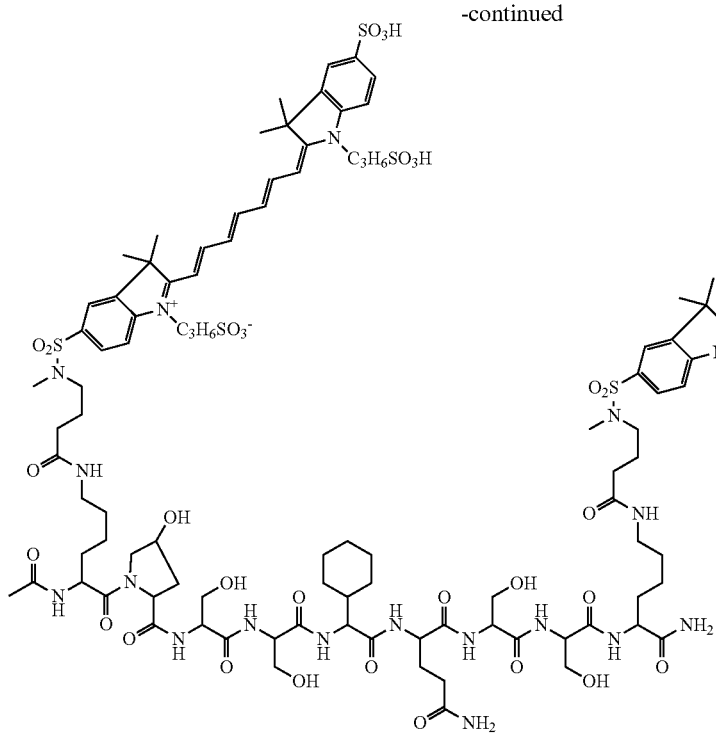

30

4. A pharmaceutical composition comprising an agent of claim 1 and a pharmaceutically acceptable excipient.

5. A method of in vivo imaging, comprising:
(a) administering to a subject an agent of claim 1;
(b) allowing the agent to distribute within the subject; and
(c) detecting a signal emitted by the prostate specific antigen activatable agent.

6. A method of imaging prostate cancer in a subject, comprising:
(a) administering an agent of claim 1 to a subject; and
(b) detecting the presence of the agent;
(c) producing an image representative of the enzymatically active prostate specific antigen, thereby imaging the presence of prostate cancer.

7. A method of in vitro imaging, comprising:
(a) contacting a sample with an agent of claim 1;
(b) allowing the agent to bind to a biological target; and
(c) detecting a signal emitted from the agent to determine whether the agent has been activated by or bound to the biological target.

8. The agent of claim 1, wherein F is represented by

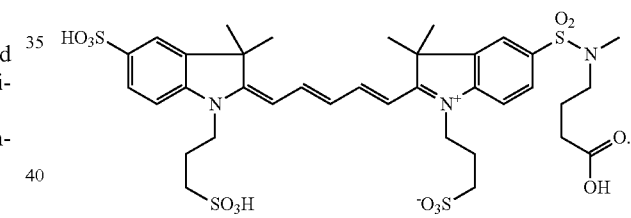

9. The agent of claim 1, wherein F is represented by

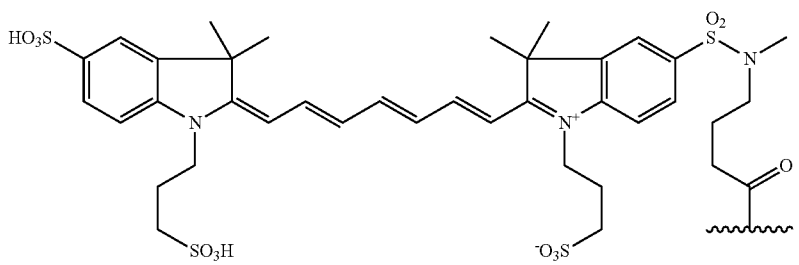

10. The agent of claim 1, wherein $R^1$ is —($C_{1-6}$ alkylene)-N($R^*$)C(O)—($C_{1-6}$ alkylene)-N(—($C_{1-6}$ alkylene)-methoxypolyethylene glycol))C(O)—($C_{1-6}$ alkylene)-methoxypolyethylene glycol.

11. The agent of claim 1, wherein $R^1$ is
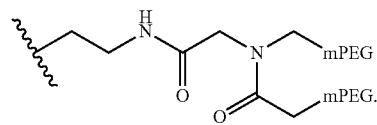
12. The agent of claim 1, wherein $R^1$ is about 40 kDa.
* * * * *

SEQUENCE LISTING

```
<160> NUMBER OF SEQ ID NOS: 47

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine
```

```
<400> SEQUENCE: 1

Lys Pro Ser Ser Gly Gln Ser Ser Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 2

Gly Pro Ala Ser Gly Gln Ser Ser Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 3

Gly Pro Ala Ser Gly Gln Ser Ser Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 4

Pro Ser Ser Gly Gln Ser Ser Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 5

Lys Pro Ser Ser Gly Gln Ser Ser Lys
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 6

Lys Pro Ala Ser Gly Gln Ser Ser Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: cyclohexylglycine

<400> SEQUENCE: 7

Gly Ser Ser Gly Gln Ser Ser Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Ser Phe Gln Ser Ser Lys
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Lys Ala Ser Phe Gln Ser Leu Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (3)..(3)
<223> OTHER INFORMATION: cyclohexylglycine

<400> SEQUENCE: 10

Pro Ser Gly Gln Ser Lys
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline

<400> SEQUENCE: 11

Lys Pro Ser Ser Phe Gln Ser Ser Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: cyclohexylglycine

<400> SEQUENCE: 12

Gly Ala Ser Gly Gln Ser Ser Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine
```

```
<400> SEQUENCE: 13

Gly Pro Ser Ser Gly Gln Ser Ser Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 14

Pro Ser Ser Gly Gln Ser Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 15

Pro Ala Ser Gly Gln Ser Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 16

Pro Ala Ser Gly Gln Ser Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: cyclohexylglycine

<400> SEQUENCE: 17

Ser Ser Gly Gln Ser Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: cyclohexylglycine

<400> SEQUENCE: 18

Ser Ser Gly Gln Ser Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 19

Pro Ser Ser Gly Gln Ser Ser
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 20

Pro Ala Ser Gly Gln Ser Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 21

Pro Ala Ser Gly Gln Ser Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: cyclohexylglycine

<400> SEQUENCE: 22

Ser Ser Gly Gln Ser Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: cyclohexylglycine

<400> SEQUENCE: 23

Ser Ser Gly Gln Ser Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ser Phe Gln Ser Leu
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ser Phe Gln Ser Leu
1               5
```

```
<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: cyclohexylglycine

<400> SEQUENCE: 26

Ser Gly Gln Ser
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: cyclohexylglycine

<400> SEQUENCE: 27

Ser Gly Gln Ser
1

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline

<400> SEQUENCE: 28

Pro Ser Ser Phe Gln Ser Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline

<400> SEQUENCE: 29

Pro Ser Ser Phe Gln Ser Ser
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                peptide
<220> FEATURE:
<221> NAME/KEY: MOD_RES
<222> LOCATION: (3)..(3)
<223> OTHER INFORMATION: cyclohexylglycine

<400> SEQUENCE: 30

Ala Ser Gly Gln Ser Ser
 1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: cyclohexylglycine

<400> SEQUENCE: 31

Ala Ser Gly Gln Ser Ser
 1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 32

Pro Ser Ser Gly Gln Ser Ser
 1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 33

Pro Ser Ser Gly Gln Ser Ser
 1               5

<210> SEQ ID NO 34
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 34

Ala Ser Phe Gln Ser Ser
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ser Phe Gln Ser Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 36

Lys Pro Ser Ser Gly Gln Ser Ser Lys
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 37

Gly Pro Ala Ser Gly Gln Ser Ser Lys
1               5

<210> SEQ ID NO 38
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 38

Gly Pro Ala Ser Gly Gln Ser Ser Lys
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 39

Lys Pro Ser Ser Gly Gln Ser Ser Lys
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline
<220> FEATURE:
<221> NAME/KEY: MOD_RES
<222> LOCATION: (4)..(4)
<223> OTHER INFORMATION: cyclohexylglycine

<400> SEQUENCE: 40

Pro Ser Ser Gly Gln Ser Ser Lys
1               5

<210> SEQ ID NO 41
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 41

Lys Pro Ala Ser Gly Gln Ser Ser Lys
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline

<400> SEQUENCE: 42

Lys Pro Ser Ser Phe Gln Ser Ser Lys
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: hydroxyproline

<400> SEQUENCE: 43

Pro Ala Ser Phe Gln Ser Ser Lys
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 44

Gly Pro Ser Ser Gly Gln Ser Ser Lys
1               5

<210> SEQ ID NO 45
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 45

Lys Pro Ser Ser Gly Gln Ser Ser Lys
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 46

Lys Pro Ser Ser Gly Gln Ser Ser Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hydroxyproline
<220> FEATURE:
<221> NAME/KEY: MOD_RES
<222> LOCATION: (5)..(5)
<223> OTHER INFORMATION: cyclohexylglycine

<400> SEQUENCE: 47

Gly Pro Ser Ser Gly Gln Ser Ser Lys
1               5
```